United States Patent
Brosnan et al.

(10) Patent No.: US 10,403,401 B2
(45) Date of Patent: Sep. 3, 2019

(54) MEDICAL APPARATUS WITH SELECTIVELY ENABLED FEATURES

(71) Applicant: Stryker Corporation, Kalamazoo, MI (US)

(72) Inventors: Daniel Vincent Brosnan, Kalamazoo, MI (US); Richard A. Derenne, Portage, MI (US); Martin W. Stryker, Kalamazoo, MI (US); Richard C. Mayoras, Jr., Kalamazoo, MI (US); Thomas Joseph Durlach, Kalamazoo, MI (US)

(73) Assignee: Stryker Corporation, Kalamazoo, MI (US)

(*) Notice: Subject to any disclaimer, the term of this patent is extended or adjusted under 35 U.S.C. 154(b) by 609 days.

(21) Appl. No.: 14/945,220

(22) Filed: Nov. 18, 2015

(65) Prior Publication Data
US 2016/0140307 A1 May 19, 2016

Related U.S. Application Data

(60) Provisional application No. 62/081,744, filed on Nov. 19, 2014.

(51) Int. Cl.
*G06F 19/00* (2018.01)
*A61B 5/0402* (2006.01)
(Continued)

(52) U.S. Cl.
CPC ............ *G16H 40/63* (2018.01); *A61G 7/018* (2013.01); *A61G 7/0524* (2016.11); *A61H 23/006* (2013.01); *A61H 23/02* (2013.01); *G06F 19/00* (2013.01); *G06F 19/3456* (2013.01); *G07F 17/0042* (2013.01); *A61B 5/0205* (2013.01); *A61B 5/6891* (2013.01); *A61G 7/005* (2013.01);
(Continued)

(58) Field of Classification Search
CPC ............... H04L 2209/88; H04L 63/101; G06F 19/3418; G06F 19/326; G06F 19/3468; G06F 21/602; G06F 19/00; G06Q 10/10; G06Q 10/06; G06Q 20/145; G06Q 50/24; G16H 40/20; G16H 40/67; G16H 80/00; G16H 10/60; G16H 10/65; A61F 7/00
See application file for complete search history.

(56) References Cited

U.S. PATENT DOCUMENTS

| | | |
|---|---|---|
| 5,062,151 A | 10/1991 | Shipley |
| 5,699,038 A | 12/1997 | Ulrich et al. |

(Continued)

FOREIGN PATENT DOCUMENTS

| | | |
|---|---|---|
| EP | 1199027 A2 | 4/2002 |
| EP | 1623666 B1 | 2/2006 |

(Continued)

*Primary Examiner* — Maroun P Kanaan
(74) *Attorney, Agent, or Firm* — Warner Norcross + Judd LLP

(57) ABSTRACT

A medical system includes a medical apparatus, a computer, a user input device, and at least one feature in communication with and controlled by the computer. The computer is in communication with the user input device, which is configured and arranged to allow a user to purchase the use of the feature. The computer is configured to enable the use of the feature after the user purchases use of the feature.

23 Claims, 13 Drawing Sheets

(51) Int. Cl.
*A61H 7/00* (2006.01)
*G16H 40/63* (2018.01)
*A61G 7/018* (2006.01)
*A61H 23/02* (2006.01)
*A61H 23/00* (2006.01)
*A61G 7/05* (2006.01)
*G07F 17/00* (2006.01)
*A61B 5/00* (2006.01)
*A61G 7/012* (2006.01)
*A61G 7/005* (2006.01)
*A61B 5/0205* (2006.01)
*A61H 9/00* (2006.01)

(52) U.S. Cl.
CPC ............ *A61G 7/012* (2013.01); *A61H 9/0078* (2013.01); *A61H 2201/0103* (2013.01); *A61H 2201/0142* (2013.01); *A61H 2201/0207* (2013.01); *A61H 2201/5002* (2013.01); *A61H 2201/502* (2013.01); *A61H 2201/5012* (2013.01); *A61H 2201/5043* (2013.01); *A61H 2201/5046* (2013.01); *A61H 2201/5061* (2013.01); *A61H 2201/5071* (2013.01); *A61H 2201/5082* (2013.01); *A61H 2201/5092* (2013.01); *A61H 2201/5097* (2013.01); *A61H 2209/00* (2013.01); *A61H 2230/06* (2013.01); *A61H 2230/207* (2013.01); *A61H 2230/25* (2013.01); *A61H 2230/30* (2013.01); *A61H 2230/40* (2013.01)

(56) References Cited

U.S. PATENT DOCUMENTS

| | | |
|---|---|---|
| 5,917,425 A | 6/1999 | Crimmins et al. |
| 6,017,354 A | 1/2000 | Culp et al. |
| 6,612,985 B2 | 9/2003 | Eiffert et al. |
| 7,638,958 B2 | 12/2009 | Philipp et al. |
| 7,746,218 B2 | 6/2010 | Collins, Jr. et al. |
| 8,535,342 B2 | 9/2013 | Malackowski et al. |
| 8,887,272 B2 | 11/2014 | Urness et al. |
| 2002/0084903 A1 | 7/2002 | Chaco |
| 2002/0145534 A1 | 10/2002 | Dempsey |
| 2002/0167417 A1 | 11/2002 | Welles, II et al. |
| 2014/0115784 A1* | 5/2014 | Johannigman ........... A61G 7/00 5/600 |
| 2014/0249658 A1* | 9/2014 | Curry .................... G05B 15/02 700/90 |
| 2015/0105636 A1 | 4/2015 | Hayman et al. |

FOREIGN PATENT DOCUMENTS

| | | |
|---|---|---|
| EP | 2725507 B1 | 10/2016 |
| WO | 199834577 A1 | 8/1998 |
| WO | 2001085085 A2 | 11/2001 |
| WO | 2003105095 A2 | 12/2003 |
| WO | 2004093023 A2 | 10/2004 |
| WO | 2004104619 A1 | 12/2004 |
| WO | 2011113070 A1 | 9/2011 |

\* cited by examiner

MEDICAL APPARATUS WITH SELECTIVELY ENABLED FEATURES

CROSS-REFERENCE TO RELATED APPLICATION

This application claims the benefit of U.S. Provisional Patent Application No. 62/081,744, filed Nov. 19, 2014, which is incorporated herein by reference in its entirety and commonly owned by Stryker Corporation of Kalamazoo, Mich.

TECHNICAL FIELD AND BACKGROUND

The present disclosure relates to a medical apparatus—such as a bed, a stretcher, a cot, a medical chair, an operating room table, a temperature management device, medical tools or equipment, and other medical devices—and, more particularly, to the electronics and communication systems on board or in communication with the medical apparatus for authorizing, managing, tracking, monitoring, controlling, or using features, such as software, hardware, or devices, at or near the medical apparatus whether resident on the medical apparatus or uploaded or added to the medical apparatus.

SUMMARY

The present disclosure provides systems and methods for authorizing, managing, tracking, monitoring, controlling, or using one or more features at a medical apparatus whether resident or not on the medical apparatus.

In some embodiments, a system includes a medical apparatus, a computer, and at least one feature (resident at the medical apparatus or not) that is stored in or in communication with and controlled by the computer. The computer is in communication with a user input device that allows a user to select the use of the feature. After receiving authorization for the use, the computer enables the use of the feature. For example, authorization may include payment or an agreement to pay by the user or a third party, such as an insurance company, or a prescription by a caregiver.

In other embodiments, a system includes a medical apparatus and a computer. The medical apparatus includes at least one feature that is stored in or in communication with and controlled by the computer. The computer is in communication with a user input device that allows a user to select the feature and, further, to agree to pay or to purchase the use of the feature, with the computer enabling the use of the feature after the user agrees to pay or purchases use of the feature.

For example, the user input device may allow the user to make direct payment, for example, through a credit card, or may authorize billing to the user, for example, by a hospital or by a third party.

In some embodiments, a system includes a medical apparatus and a computer. The medical apparatus includes at least one feature that is stored in or in communication with and controlled by the computer. The computer is in communication with a user input device that allows a healthcare person to generate a prescription to prescribe the use or prohibit the use of the feature. In response to the prescription, the computer enables or disables use of the feature.

In some embodiments, a system includes a medical apparatus and a computer. The medical apparatus includes at least one feature that is stored in or in communication with the computer. The computer is in communication with a user input device that allows a person to select use of the feature and to control the feature. The user input device generates an enable signal to the computer in response to input from the person, with the computer enabling use of the feature in response to the enable signal. The user input device also generates a control signal to the computer in response to input from the person, with the computer controlling use of the feature in response to the control signal. In addition, the computer monitors the enablement of the feature and generates a confirmatory signal when the feature is enabled.

Optionally, the computer monitors the use of the feature and generates a use information signal about the use of the feature. In a further aspect, the use information signal is communicated by the system to a remote location. For example, the remote location may be a hospital network or may be a network of third party, including, for example, the Cloud service.

Further, the feature may apply treatment to a patient. The system may further include one or more sensors for monitoring information about the patient. For example, the sensor may monitor a patient's temperature, weight, incontinence, vital signs, such as blood pressure, heart rate, respiration, and $SpO_2$, or the like. The sensor is in communication with the computer, with the computer monitoring the sensor to monitor and collect information about the patient. The computer further generates a patient information signal based on the information collected by the computer about the patient.

In one aspect, the patient information signal is communicated by the system to a remote location along with the use information signal. For example, the remote location may be a hospital network or may be a network of third party, including for example the Cloud service.

Optionally, the user input devices may be resident at the medical apparatus or may be remote from the medical apparatus but configured to communicate with the computer either wirelessly or through a wired connection. For example, the user input devices may communicate with the computer through a network.

In each case, the medical apparatus may comprise a patient support, such as a hospital bed. The feature may be a patient monitoring device, including a sensor, such as a vital signs sensor, for example, a load cell, for monitoring the vital signs of a patient, an EKG, a pulse oximeter, or the like. The feature may be a sensor, such as a load cell, for monitoring patient activity, including a bed exit system. The feature may be a sensor, such as a pressure sensor, or depth sensor for monitoring interface pressure at the surface or envelopment into the surface of the patient support.

Alternately, the feature may be an entertainment device, such as a TV, a hand-held electronic device, such as a tablet, a phone, an iPod, or the like, with the feature in communication with the computer so that the computer can enable use of the device and monitor use of the device, for example, for billing purposes. In another embodiment, the feature is a software application or a file on an entertainment device, such as sound file, a game file, or video file.

Alternately, the feature may be a treatment device, such as turning device, a percussion and/or vibration device, a temperature management device, such as a pump and/or a warming or cooling blanket or pad, a vacuum assisted device, or a hyperbaric device for delivering oxygen.

In yet another form, the feature may be a sensor for monitoring the status of a patient support component, such as the position of a side rail, the head of bed angle, the height of the bed, the patient support deck configuration.

In another embodiment, a system includes a medical apparatus and a computer. The medical apparatus includes at least one feature that is stored in or in communication with the computer and controlled by the computer. The computer is also in communication with a user input device that allows a person to select use of the feature. The user input device generates an enable signal to the computer in response to input from a user to enable use of the feature. The computer generates a transaction signal associated with the enablement of the feature, which may be used to bill for the use of the feature, charge for the use of the feature, or request approval before the use of the feature.

Optionally, the transaction signal comprises a request for prepayment associated with the use of the feature before the feature is enabled by the computer or an invoice for billing associated with the use of the feature.

For example, the medical apparatus may comprise a patient support apparatus, such as a hospital bed, with the computer integrated into the patient support. The feature may be an entertainment device, such as a TV, a hand held electronic device, such as a tablet, a phone, an iPod, or the like, or a file for uploading to an entertainment device, with the feature in communication with the computer so that the computer can enable use of the device or file and monitor use of the device or file, for example, for billing purposes. For example, the computer may be in communication with a network server that is configured to upload the file to the computer upon a request from the computer.

Alternately, the feature may be a treatment device or monitoring device, such as described above.

In some embodiments, the computer that acts as a thin client for at least one network service, thereby enabling uploading, upgrades, modifications, improvements, and customizations of the one or more features at the medical apparatus. The network service may provide information, algorithms, data processing, and/or other features for the medical apparatus that relate to such features as: monitoring patient movement (including turns), providing patient care assessments, implementing a patient care protocol, monitoring maintenance needs, analyzing sensor data, and implementing an exit alert system.

The computer may forward information data to the network service for processing and receive processed data back from the network service, wherein the processed data is a result of the processing of the signals received from the computer. The forwarded information data may include information generated from one or more sensors, such as a plurality of force sensors. For example, such information may enable the network service to determine information about a patient's condition, including whether or not the patient has turned while positioned on the patient support apparatus, whether a patient may be about to exit from the patient support apparatus, and/or whether a patient on the patient support apparatus is asleep or awake.

The network service and/or local application may generate billing information based on usage of the feature of the patient support apparatus. The network service and/or local application may alternatively provide information relating to how often a patient supported on the patient support apparatus should be turned, and/or other information relating to a patient care protocol.

The network service may communicate with at least one other network service on the remote network. The other network service may be any one or more of the following: an electronic medical records service; a caregiver workflow service; an admission, discharge and tracking (ADT) service; a real time location service; a billing and accounting service; and/or a caregiver communication service.

In some embodiments, a system includes a medical apparatus and a computer. The computer is in communication with a remote store that includes downloadable applications for use at the medical apparatus. The system is configured to associate a patient with the medical apparatus and to download from the remote store a software application for use at the medical apparatus based on information about the patient.

The application may be a health-based application, e.g. related to monitoring the vital signs of a patient, relating to fall prevention, displaying of EMR/EHR information, displaying an X-ray, or may be entertainment based, e.g. playing of music or playing of videos or movies.

In some embodiments, the application may have levels of functionality. Further, the computer may control or select which level of the application is going to be used or be available based on further input to or information stored in the computer, such as a user's credentials. The user's credentials may be input by the user or detected by the computer. For example, the user may wear a near field tag, such as an RFID tag, which when detected by the computer identifies to the computer the user's ID, and optionally who the user is and/or their credentials. Alternately, the computer may read or retrieve information about the user based on the user's ID from an electronics records system, such as a hospital network, an Emergency Medical Records (EMR) system, an Emergency Hospital Records (EHR) system, a Workflow system, an admission, discharge and transfer (ADT) system, a third party server, or a Cloud service.

In other embodiments, the association between the patient and the medical apparatus may be based on input, either locally or remotely, into the computer or detected by the computer. For example, when a patient is assigned to a room and/or to a medical apparatus, such as when the patient is first admitted to the hospital, the patient is electronically associated with the medical apparatus. Once the association is forwarded to the computer, the computer is programmed to automatically download/install the application or applications needed for proper care of the patient.

The download may be automatically done at the time the patient is first assigned to the room and/or to a medical apparatus and the information about the patient's needs is transmitted to or read by the computer. Alternately, the download may occur based on a status or a change in status of the patient. For example, the status may be determined by reading or receiving information about the patient, such as by reading or receiving information from an electronic records system, such as from an EMR/EHR system; reading or receiving information from other hospital systems, such as a nurse call system, a patient work flow system, an admission, discharge and transfer (ADT) system; reading or receiving information from a third party server or Cloud service; and/or by the output from another application(s) or a combination of the above.

In some embodiments, the computer is in communication with a user input device that allows a caregiver to associate the patient with and input the patient's condition into the medical apparatus. The user input device generates an association signal to the computer in response to input from the caregiver, with the computer downloading the application in response to the association signal. Optionally, the user input device may be resident at the medical apparatus or may be remote from the medical apparatus but configured to communicate with the computer either wirelessly or through a wired connection. For example, the user input device may communicate with the computer through a hospital network.

Optionally, the computer monitors the use of the application and generates a use information signal about the use of the feature. In a further aspect, the use information signal is communicated by the system to a remote location. For example, the remote location may be a hospital network or may be a network of third party, including, for example, a Cloud service.

In some embodiments, the medical apparatus includes a store interface that allows a user to select an application for download to the medical apparatus. For example, the computer may include or be in communication with a display with user input devices, such as buttons or touch sensitive areas of the display, that provide the store interface, which allows a user to select and access the downloaded application.

Optionally, the computer or the interface controls the availability of the application based on a parameter—for example—a parameter of the end-user. In one aspect, the parameter is the security level of the end user, for example, whether the end user is a patient, nurse, physician or other caregiver. In another aspect, the parameter is the skill or training level of the user.

In some embodiments, the user interface may be a separate device from the medical apparatus, such as a phone, a watch, a tablet, a desktop or laptop computer, or a secondary medical device, which is securely connected to the medical apparatus, or may comprise a display at the medical apparatus that is mirrored to another device, such as a phone, a watch, a tablet, a desktop or laptop computer, or a secondary medical device.

In each case, the medical apparatus may comprise a patient support, such as a hospital bed, or a medical treatment apparatus, such as ventilation equipment, a pressure cuff assembly, such as DVT assembly, a hyperbaric treatment or vacuum treatment device, a medical instrument, such as a surgical tool, or the like. The application may be an application for a patient monitoring device, including a sensor, such as a vital signs sensor, for example, a load cell for monitoring the vital signs of a patient, an EKG, a pulse oximeter, or a sensor, such as a load cell, for monitoring patient activity, including a bed exit system, or a pressure sensor or depth sensor for monitoring interface pressure at the surface or envelopment into the surface of a patient support.

Alternately, as noted, the application may be a file, such as sound file, a game file, or video file, for downloading to an entertainment device or enable a device to provide entertainment, such as a TV, a hand-held electronic device, such as a tablet, a phone, an iPod, or the like, or an application that can enable use of the device via an interface at the apparatus, such as at the user or patient interface.

In some embodiments, a system includes a medical apparatus and a computer with a user interface for controlling one or more features at the medical apparatus. The computer is configured to configure, modify, and/or limit the user interface or functionality of the user interface based on a condition of the patient or staff and/or based on a specific care condition.

For example, the condition may be read by or transmitted to the computer. The conditions, for example, include the type or acuity of the patient, level or type of experience of the caregiver, level or type of experience of the hospital, level or type of the facility protocols or specifications, etc.

In one embodiment, a user logs in to the apparatus to associate the user to the apparatus or logs-in a patient to associate the patient with the apparatus.

In some embodiments, the computer determines a patient-specific condition and associated hospital protocols then activates a bed monitoring feature, such as an iBed Awareness system available from Stryker Corporation of Kalamazoo, Mich., based on those conditions.

In some embodiments, the computer determines a patient-specific condition and associated hospital protocols then downloads settings and device configurations based on those conditions.

In some embodiments, the computer re-configures the user interface and usage characteristics based on a specific care condition and/or interfaces with a $3^{rd}$ party system. For example, the computer may configure the medical apparatus to add additional functionality, e.g. a generic bed as a MedSurg bed or ICU bed.

In some embodiments, a system includes a medical apparatus and a computer that is configured to download and execute a $3^{rd}$ party user-interface and/or other application on the apparatus.

In some embodiments, the user interface may be a separate device from the medical apparatus, such as a phone, a watch, a tablet, a desktop or laptop computer, or a secondary medical device, which is securely connected to the medical apparatus, or may comprise a display at the medical apparatus that is mirrored to another device, such as a phone, a watch, a tablet, a desktop or laptop computer, or a secondary medical device.

In each case, the medical apparatus may comprise a patient support, such as a hospital bed, or a medical treatment apparatus, such as ventilation equipment, a pressure cuff assembly, such as DVT assembly, a hyperbaric treatment or vacuum treatment device, a medical instrument, such as a surgical tool, or the like. The feature may be an application for a patient monitoring device, including a sensor, such as a vital signs sensor, for example, a load cell for monitoring the vital signs of a patient, an EKG, a pulse oximeter, or a sensor, such as a load cell, for monitoring patient activity, including a bed exit system, or a pressure sensor or depth sensor for monitoring interface pressure at the surface or envelopment into the surface of a patient support.

In each case the computer may form the control system for the medical apparatus or may form part of the control system for the medical apparatus.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and is capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

DETAILED DESCRIPTION OF THE EMBODIMENTS

Figure 1:
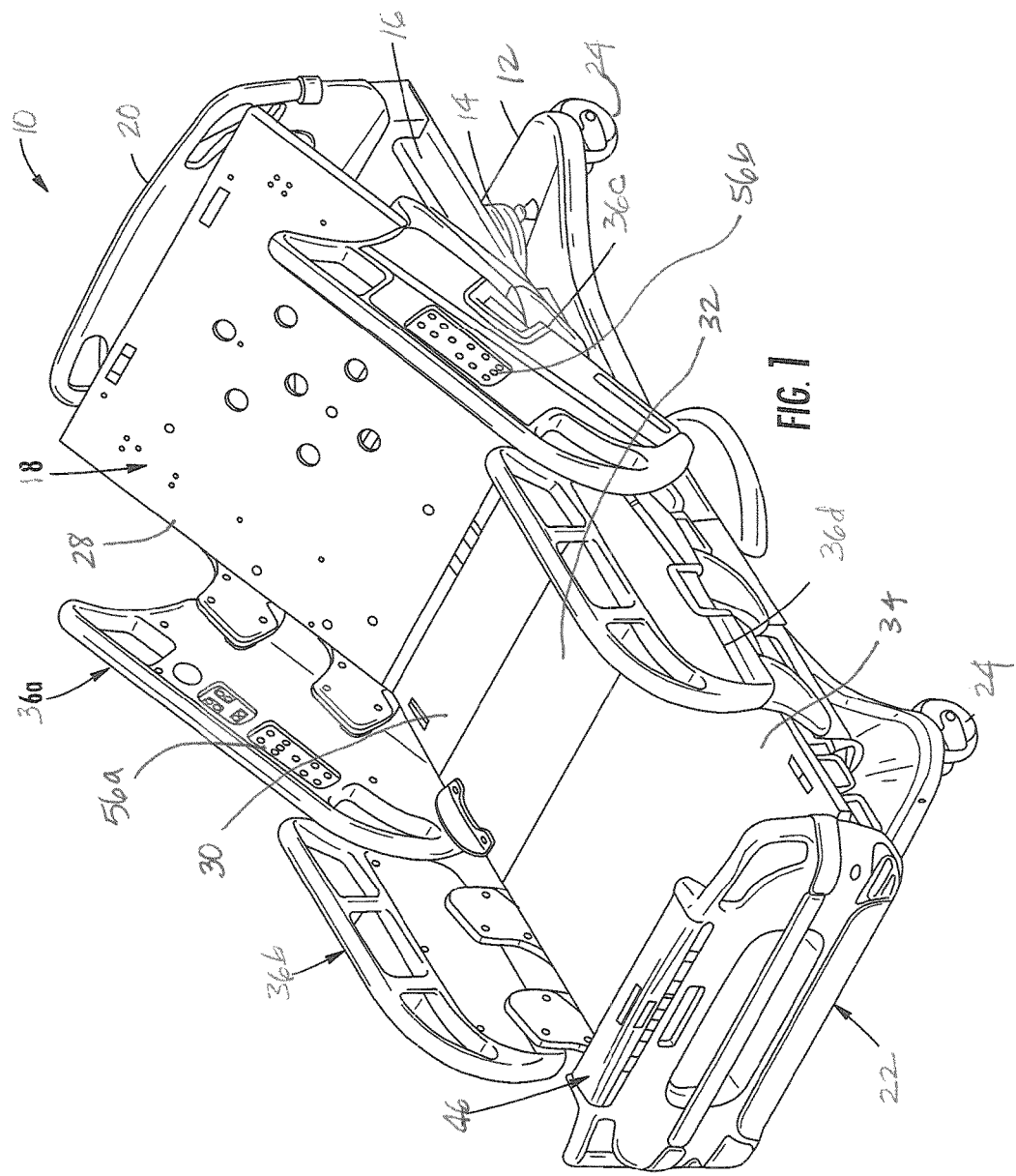
FIG. 1 is a perspective view of an illustrative medical apparatus that is able to implement any one or more of the various features of the present invention.

Referring to FIG. 1, the numeral 10 generally designates a medical apparatus in the form of a patient support apparatus that includes a control system (50, FIG. 2) with electronics and a communication system for authorizing, managing, tracking, monitoring, uploading, downloading, controlling, or using software or hardware or devices at or near apparatus 10. In the illustrated embodiment, apparatus 10 is a hospital bed, including an intensive care (ICU) bed, MedSurg bed, or a maternity bed; however, it should be understood that the medical apparatus may comprise other apparatuses, such as a stretcher, cot, chairs, including a medical recliner, an operating room table, and other medical apparatuses, such as medical tools or instruments or treatment devices, including temperature management apparatuses or the like.

Referring again to FIG. 1, patient support apparatus 10 includes a base 12, a pair of elevation adjustment mechanisms 14, a frame or litter assembly 16, a deck 18 which forms part of the patient support surface, a headboard 20, and a footboard 22. For example, base 12 may include caster wheels 24 that can be selectively locked and unlocked so that, when unlocked, patient support apparatus 10 is able to be wheeled to different locations. Elevation adjustment mechanisms 14 are adapted to raise and lower frame 16 with respect to base 12. Elevation adjustment mechanisms 14 may be hydraulic actuators, electric actuators, or any other suitable device for raising and lowering frame 16 with respect to base 12. In some embodiments, elevation adjustment mechanisms 14 operate independently so that the orientation of frame 16 with respect to base 12 may also be adjusted between, for example, a Trendelenburg ("Trend") position and a reverse Trendelenburg ("reverse Trend") position.

Frame 16 provides a structure for supporting deck 18, headboard 20, and footboard 22. Deck 18 provides a surface on which a mattress, or other cushion, is positionable so that a patient may lie and/or sit thereon. Deck 18 may be made of a plurality of sections, some of which are pivotable about generally horizontal pivot axes. In the illustrated embodiment shown in FIG. 1, deck 18 includes a head section 28, a seat section 30, a thigh section 32, and a foot section 34. Head section 28, which is also sometimes referred to as a Fowler section, is pivotable between a generally horizontal orientation (not shown in FIG. 1) and a plurality of raised positions (one of which is shown in FIG. 1). Thigh section 32 and foot section 34 may also be pivotable in some embodiments. In addition, patient support apparatus 10 may include four side rails: a right head side rail 36a, a right foot side rail 36b, a left head side rail 36c, and a left foot side rail 36d. Side rails 36 are movable between a raised position (such as the configuration shown in FIG. 1) and a lowered position.

For examples of the construction of base 12, elevation adjustment mechanisms 14, frame 16, deck 18, headboard 20, footboard 22, and/or side rails 36 reference is made to U.S. Pat. No. 7,690,059 issued to Lemire et al., and entitled HOSPITAL BED, the complete disclosure of which is incorporated herein by reference; or as disclosed in commonly assigned U.S. Pat. No. 8,689,376, commonly owned by Stryker Corp. of Kalamazoo, Mich., the complete disclosure of which is also hereby incorporated herein by reference; or as embodied in the commercially available S3 bed sold by Stryker Corporation of Kalamazoo, Mich., and document in the Stryker Maintenance Manual for Stryker's MedSurg Bed, Model 3002 S3, (doc. 3006-109-002 Rev D), published in 2010, the complete disclosure of which is also hereby incorporated herein by reference. However, it should be understood that the construction of base 12, elevation adjustment mechanisms 14, frame 16, deck 18, headboard 20, footboard 22 and/or side rails 36 may also take on forms different from what is disclosed in these documents.

Figure 2:
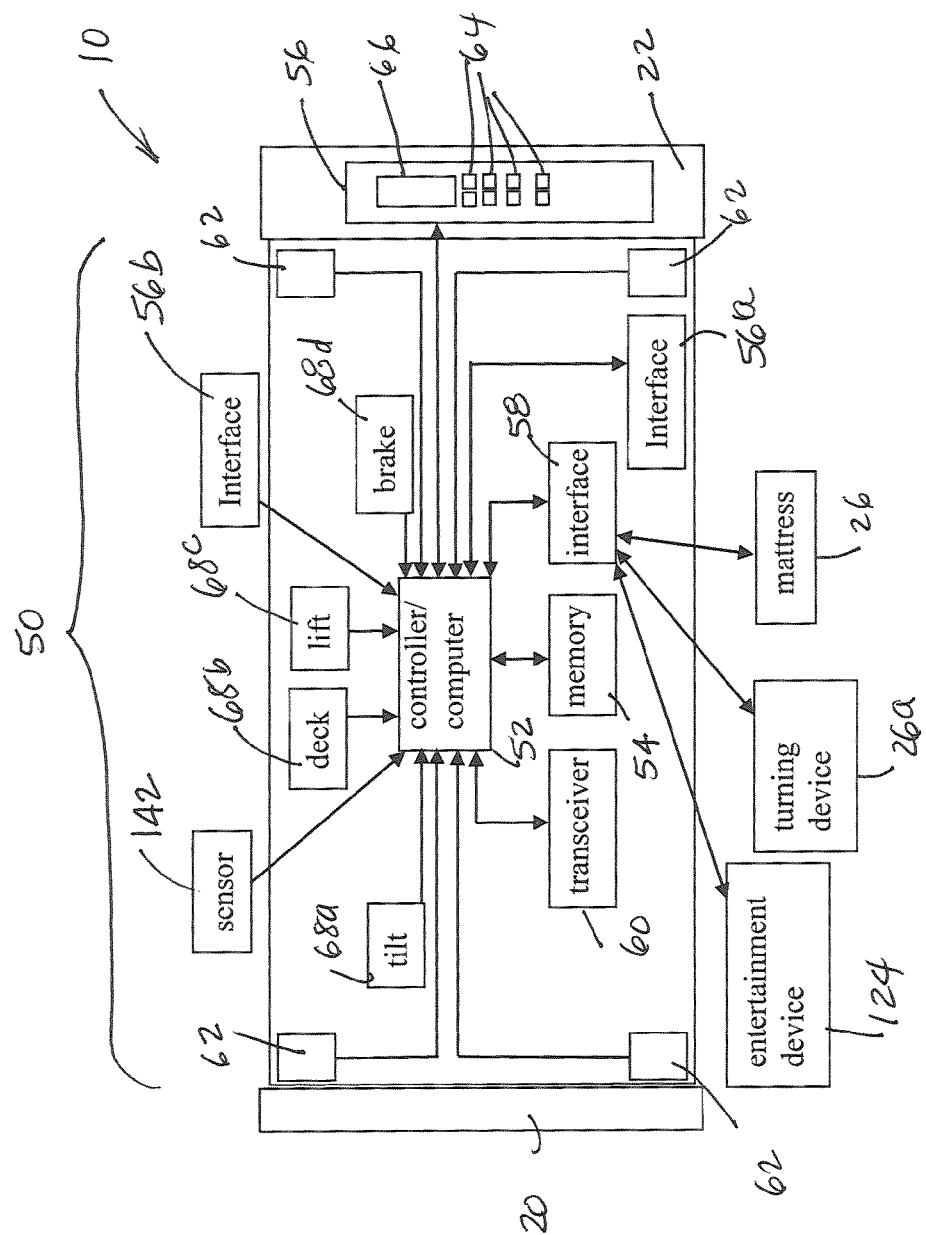
FIG. 2 is a diagram of a control system according to one embodiment that may be implemented into various medical apparatuses, such as, but not limited to, the one of FIG. 1.

Referring to FIG. 2, the numeral 50 generally designates a control system for patient support apparatus 10. As will be more fully described below, control system 50 is configured to allow features at the patient support apparatus or in proximity to the patient support apparatus to be enabled, or downloaded in the case of software, based on input at the patient support apparatus or input remote from the patient support apparatus. The input may, for example, be in the form of an authorization, such as a prescription from a healthcare person or a provider or an accounting authorization, including an accounting authorization from the accounting department of the hospital accounting department, a credit card company, a bank, or from a user who authorizes payment or billing. The term "healthcare provider or person" is intended to be broadly construed and includes anyone involved in the care of a patient, and, therefore, includes physicians, PAs, nurses, and attendants or the like.

For example, such features may include software, hardware, or devices resident or not resident at the bed. Software may include control software for: Controlling a device or component of or near the apparatus 10; or monitoring software for monitoring a device or component of apparatus 10, patient activity, patient environment (room temperature, lighting, interaction with others), patient health by way of a patient monitoring device, or care or treatment of a patient.

For example, the monitoring software may monitor device performance (e.g. Fowler section cycles), patient activity, including potential or actual bed exits, how many times or when a patient was visited by a healthcare person (for example, through near field tags, such as RFID tags, worn by a healthcare person), how many times or when a patient was turned, or how many times or when a patient was given percussion or vibration treatment, for example. Hardware may include sensors that detect temperature, moisture, pressure, immersion into the patient support surface (e.g. mattress), patient activity, patient health, or care or treatment of a patient. Devices may include treatment devices, diagnostic devices, and patient monitoring devices, as well as entertainment or communication devices.

As best seen in FIG. 2, control system 50 includes a controller 52, a memory 54 in communication with the controller 52, a user input device or interface 56, at least one sensor or device interface 58, and at least one transceiver 6. Together all of these components or some of these components form a computer in the broad sense. Control system 50 also includes other sensors, for example, sensors for detecting the position of the side rails, the status of caster brakes, the positions of the deck section, or the height of the deck, for example. Optionally, control system 50 may also include load cells 62 for weighing the patient and/or as part of a bed exit system. In the illustrated embodiment shown in FIG. 2, control system 50 further includes a plurality of actuators 68, such as a tilt actuator 68a, a deck actuator 68b, a lift actuator 68c, and a brake actuator 68d. Other actuators may also be included.

The components of control system 50 communicate with each other using conventional electronic communication techniques. In one embodiment, controller 52 communicates with memory 54, user interface 56, and load cells 62 using I-squared-C communications. Other types of serial or parallel communication can alternatively be used. In some other embodiments, different methods may be used for different components. For example, in one embodiment, controller 52 communicates with user interface 56 via a Controller Area Network (CAN) or local Interconnect Network (LIN), while it communicates with memory 54, actuators 68, and load cells 62 using I squared C. Still other variations are possible.

User interface 56 may include a plurality of buttons 64 that a caregiver can press in order to control various features of the patient support apparatus, such as, but not limited to, raising and lowering the height of frame 16 via lift actuators 68c, pivoting one or more of support surface sections 28 via one or more deck actuators 68b, turning on and off a brake (not shown) via brake actuator 68d, controlling a scale system integrated into the patient support apparatus 10, controlling an exit alert system integrated into the support apparatus 10, and/or controlling other features of the patient support apparatus 10. User interface 56 further includes a display 66 integrated therein. Display 66 may comprise a touchscreen display capable of displaying text and/or graphics and sensing the location that a user's finger touches the display, although it will be understood that display 66 could be modified to be a normal LCD display without touchscreen capabilities that used hard or soft buttons to interact therewith, or still other types of displays. Further, as will be more fully described below, interface 56, such as display 66, may be configured to provide a menu for selecting features and icons to indicate when an application is enabled at the patient support apparatus, for example, when it has been authorized for use, or when it is disabled.

Controller 52 includes one or more microcontrollers, microprocessors, and/or other programmable electronics that are programmed to carry out the functions described herein. It will be understood that controller 52 may also include other electronic components that are programmed to carry out the functions described herein, or that support the microcontrollers, microprocessors, and/or other electronics. The other electronic components include, but are not limited to, one or more field programmable gate arrays, systems on a chip, volatile or nonvolatile memory, discrete circuitry, integrated circuits, application specific integrated circuits (ASICs) and/or other hardware, software, or firmware, as would be known to one of ordinary skill in the art. Such components can be physically configured in any suitable manner, such as by mounting them to one or more circuit boards, or arranging them in other manners, whether combined into a single unit or distributed across multiple units. Such components may be physically distributed in different positions on patient support apparatus 10, or they may reside in a common location on patient support apparatus 10. When physically distributed, the components may communicate using any suitable serial or parallel communication protocol, such as, but not limited to, CAN, LIN, Firewire, I-squared-C, RS-232, RS-485, etc.

Load cells 62 are, in some embodiments, any conventional load cells, or similar force measuring sensors, that are positioned to detect the amount of downward force exerted by patient support deck 18, and any objects, patient(s), and/or other persons that are exerting downward forces on deck 18, whether due to gravity or due to other causes. In some embodiments, the load cells 62 may be configured so that, in addition to downward forces, they are also able to detect forces exerted in generally horizontal directions (both laterally and longitudinally).

The physical arrangement of load cells 62 may take on a conventional arrangement, such as those found in a variety of different conventional hospital beds. For example, in one embodiment, the position and physical construction of load cells 62 are the same as that found in the S3® bed sold by Stryker Corporation of Kalamazoo, Mich. These physical details are described in detail in the Stryker Maintenance Manual for Stryker's MedSurg Bed, Model 3002 S3, (doc. 3006-109-002 Rev D), published in 2010, the complete disclosure of which has already been incorporated herein by reference.

Controller 52 is in communication with each of four load cells 62 and receives the outputs from load cells 62. Load cells 62 are positioned adjacent each corner of the deck 18 and cumulatively sense the entire weight of a patient, other person, and/or objects positioned on the deck 18. In one arrangement, the load cells are positioned such that one load cell 62 is positioned adjacent each corner of a load frame (not shown), and the load cells 62 detect forces exerted by a patient support frame upon the load frame (through the load cells). While the construction of the load frame and patient support frame may vary, one example is disclosed in the commonly assigned U.S. Pat. No. 7,690,059 mentioned above and incorporated herein by reference. Another example is disclosed in the Stryker Maintenance Manual for the Model 3002 S3 MedSurg Bed, which has also already been incorporated herein by reference. Other constructions of the frames and positions of the load cells may also be used.

Interface 58 may be used to communicate with one or more electronic devices that are positioned on, or in the vicinity of, patient support apparatus 10. As shown in FIG. 2, interface 58 is configured to communicate with a mattress 26 that is positionable on top of deck 18. Mattress 26 may be a mattress of the type disclosed U.S. patent Ser. Nos.

13/836,813; 14/019,353; and 14/308,131, entitled INFLATABLE MATTRESS AND CONTROL METHODS, PATIENT SUPPORT COVER, and PATIENT SUPPORT COVER, respectively, filed on Mar. 15, 2013; Sep. 5, 2013, and Jun. 18, 2014, respectively, all commonly owned by Stryker Corp. of Kalamazoo, Mich., the complete disclosures of both of which are hereby incorporated herein by reference. Such mattresses include a plurality of inflatable bladders whose inflation pressure is controllable by one or more controllers contained with the mattress. The mattress may further include a plurality of sensors used for detecting information about the status of the mattress, such as, but not limited to, one or more depth sensors, fluid pressure sensors, temperature sensors, patient interface pressures sensors, and/or humidity sensors, or may be used to detect information about the patient, such as vital signs, temperature or activity.

In addition, interface 58 may be in communication with a mattress accessory 26a, such as a turning device, for example, turning bladders, which may form part of mattress 26 or may be separate components. Other mattress accessories include a flexible pressure sensing mat, which may be positioned on top of, underneath, or integrated into, mattress 26.

Such pressure sensing mats are used to detect the interface pressures between the patient and the support surface the patient is positioned on, and can be useful for monitoring such pressures so as to avoid the development, or potential development, of bed sores. In one embodiment, a flexible pressure sensing mat of the type disclosed in commonly assigned U.S. patent Ser. No. 14/003,157, filed Mar. 2, 2012 by Stryker Corporation, and entitled SENSING SYSTEM FOR PATIENT SUPPORTS, the complete disclosure of which is hereby incorporated herein by reference. Such a flexible pressure sensing mat may forward pressure information, including but not limited to, a patient interface pressure distribution map, to controller 52, and/or any other information that is detectable by the flexible pressure sensing mat (such as, but not limited to, patient heart rate, patient respiration rate, patient position, patient orientation, patient movement—including patient turns, and other information). In this manner, apparatus 10 may have these accessories resident at the apparatus, but which may be disabled and, instead, only enabled after a user, such a healthcare person, requests that the feature be enabled, as will be more fully described below.

In some embodiments, interface 58 is a Controller Area Network connection that communicates with mattress 26 and mattress accessories 26a, while in other embodiments, interface 58 takes on other forms. In one embodiment, interface 58 is a wireless connection, such as that disclosed in commonly assigned U.S. Pat. No. 8,864,205, commonly owned by Stryker Corp. of Kalamazoo, Mich., the complete disclosure of which is hereby incorporated herein by reference.

In still other embodiments, control system 50 may include more than one interface 58, and each interface 58 may be of the same or different type (e.g. some may be wired, some may be wireless, or they both may be wired or wireless but use different communication protocols). In one embodiment, control system 50 includes a near field communications transceiver that communicates in any of the manners, and with any of the devices, disclosed in commonly assigned U.S. patent application Ser. No. 13/802,992, filed Mar. 14, 2013 by applicants Michael Hayes et al, and entitled COMMUNICATION SYSTEMS FOR PATIENT SUPPORT APPARATUSES, the complete disclosure of which is hereby incorporated herein by reference. Such a near field communications transceiver can be used for establishing associations between patient support apparatus 10 and other objects, e.g. medical devices, mattress 26, patients or caregivers wearing near field ID tags, or other items noted below.

In still other embodiments, control system 50 may include more than one interface 58, and each interface 58 may be of the same or different type (e.g. some may be wired, some may be wireless, or they both may be wired or wireless but use different communication protocols). In one embodiment, control system 50 includes a near field communications transceiver that communicates in any of the manners, and with any of the devices, disclosed in commonly assigned U.S. patent application Ser. No. 13/802,992, filed Mar. 14, 2013 by applicants Michael Hayes et al, and entitled COMMUNICATION SYSTEMS FOR PATIENT SUPPORT APPARATUSES, the complete disclosure of which is hereby incorporated herein by reference. Such a near field communications transceiver can be used for establishing associations between patient support apparatus 10 and other objects (e.g. medical devices, mattress 36, patients or caregivers wearing near field ID tags, or other items).

Such associations are forwarded to controller 52. In addition to near field communications, interface 58 may also carry out far field communications using one or more transceivers that are separate from transceiver 60. Such separate transceivers typically communicate using a separate communications protocol than that of transceiver 60. For example, in one embodiment, transceiver 60 using WiFi communications, while the one or more transceivers of interface 68 use Bluetooth and/or ZigBee communications, or other protocols.

As described above, control system 50 is configured to allow certain features at the patient support apparatus or in proximity to the patient support apparatus to be enabled based on input at the patient support apparatus or input remote from the patient support apparatus. For example, interface 58 may be used to communicate and interface with the features based on input received at controller 52. The input may, for example, be in the form of an authorization, such as a prescription from a healthcare provider or accounting authorization, including an accounting authorization from the accounting department of the hospital accounting department, a credit card company, a bank, or from a user who authorizes payment.

The features to be enabled (but disabled when not authorized for use) may include built-in features at the patient support or features that are separate from the patient support. Built-in features may include software, including for example a bed-exit system, a protocol reminder system; turning devices; sensing mats; sensors for patient monitoring, including a bed exit system, an immersion system, a pressure monitoring system, a moisture management system for decubitus care, a sleep monitoring system, a physical therapy system, for example; patient monitoring devices, such as a patient tracking system or a vital signs monitoring device, a temperature monitoring device, for example; speakers; DVT devices; entertainment devices, for example, phones, tablets, audio and video players, computers, and other communication or other entertainment devices; mattress upgrades; or the like. Non-built in or non-resident features may include: treatment devices, such as a ventilator, turning devices, warming or cooling pads, wound treatment devices, such as hyperbaric or vacuum devices; patient monitoring devices, such as sensing mats, bed exit systems, including a camera-based bed exit system, sensing units for monitoring patient physiological parameters, movement, or environmental conditions; DVT devices; and entertainment devices, for example, a TV, a phone, tablets, computers, an electronic game player, a held-held music player, and other communication or entertainment devices.

Interface 58 is in communication with the respective feature and controls the respective feature based on input from controller 52. Controller 52 may receive input from user interface 56 or from user interfaces 56a and 56b, which are mounted in, for example, the head end side rails 36a, 36c. User interface 56a may be provided on each of the inwardly facing sides of head end side rails 36a, 36c, for use by a patient. User interface 56b may be provided on each of the outwardly facing side of head end side rails 36a, 36c for use by a caregiver. As noted, interface 58 may communicate wirelessly or through a wired connection. In one embodiment, as described above, controller 52 may receive input remotely from the patient support apparatus. For example, controller 52 may receive the input from a hand held device (126, see FIG. 6), a nurse call station, or through the hospital network (more fully described below).

User interfaces 56a and 56b may be used to provide authorization to controller 52 to enable any one or more of the features noted above. For example, the patient user interface(s) 56a may be configured to allow a patient or visitor or other user (though reference will be made to the patient hereinafter) to select, for example, through a touch screen, a feature that they wish to use. It should be understood that while a touch screen is described, other user interfaces, such as buttons or other types of switches, may be used. Once a feature is selected by the patient, controller 52 may generate a prompt at, for example, the touch screen asking the patient whether they agree to pay or be billed for the use of the feature. The touch screen is optionally then configured to allow the patient to indicate for example, using a button formed by the touchscreen that the patient agrees to pay or be billed. Alternately, the patient may not be asked for authorization and instead automatically billed for the use based on a pre-authorization given for example when admitted to the facility.

Figure 3:
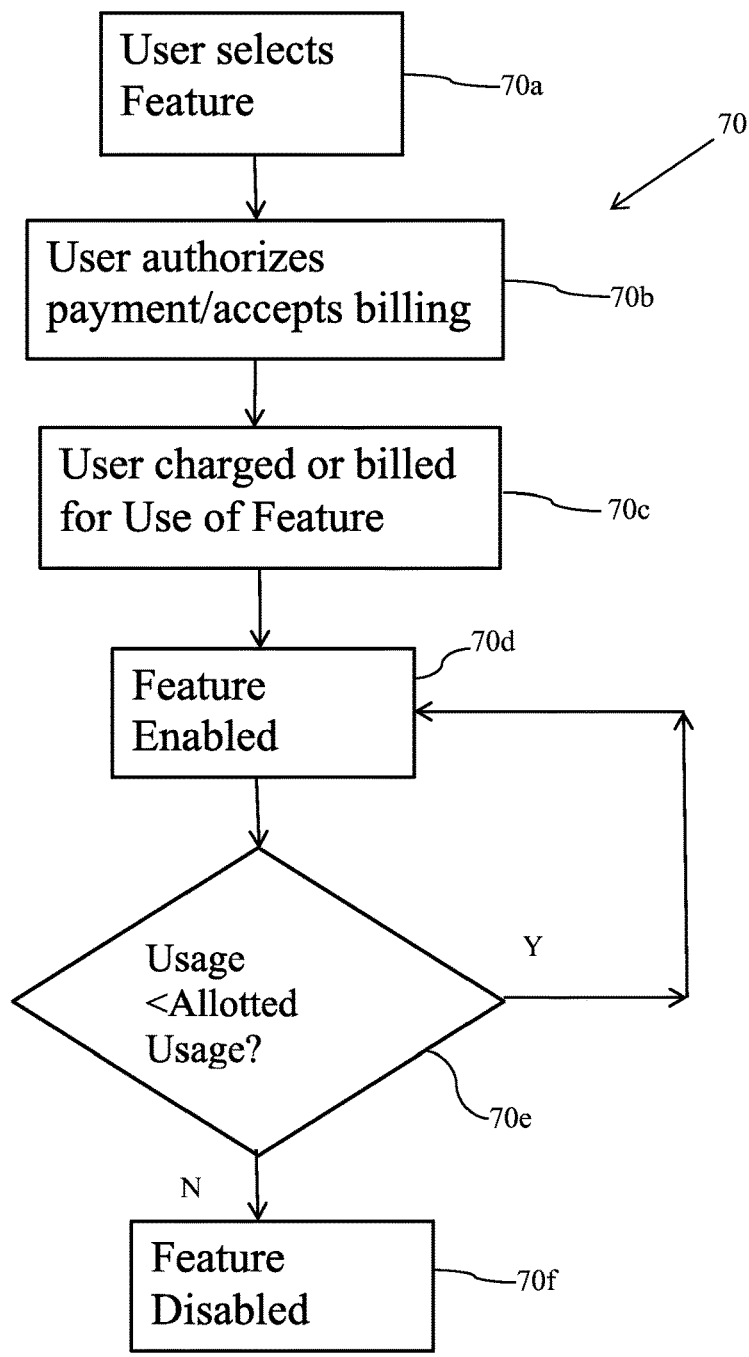
FIG. 3 is a flowchart of an illustrative authorization system that may be used to enable use of applications at the medical apparatus.

In one embodiment, as illustrated in FIG. 3, controller 52 has a software authorization algorithm 70, which begins at step 70a with the user selecting a feature using the patient user interface device 56a. The user may be prompted to authorize payment or accept billing. After the user authorizes payment or accepts billing at step 70b, an accounting signal is generated at step 70c to charge or bill the user for the use of the feature, which is then followed by the feature being enabled at step 70d. Optionally, the controller may monitor the usage of the feature at step 70e and when the usage has exceed an allotted usage, then the controller disables the feature at step 70f. For example, the controller may have a timer and disable usage after a period of time.

The payment or billing authorization by the patient can either be sent to the hospital billing department or to a credit card company or a bank via the hospital's server or directly to a credit card company or bank. Controller 52 may be configured to enable the feature simply based on the patient's agreement to pay or based on additional input, for example, approval from the hospital billing department or approval from a credit card or bank. Once the payment input (agreement to pay or approval) is received by controller 52, controller 52 will then enable the feature. For example, the controller may be configured to enable the feature for a set period of time (and then disable the feature), as noted, or may be configured to bill for the amount of usage, e.g. on an hourly basis. Alternately, the use of the features may be prepaid for, for example when the patient is admitted to the hospital, or billed simply upon selection of the feature.

In another embodiment, as described above, the authorization may be the form of a prescription. For example, when a patient is admitted to the hospital and assigned to a patient support, the patient support may include many features that that are not needed for that particular patient. Further, it may be desirable to control the use of some of the features on a patient support, for example controlling their use by a licensed health care professional by way of a prescription. Controller 52, therefore, may be configured to enable a feature only after receiving a prescription. For example, the prescription may be provided in the form of an authorization signal, which may be generated at the patient support or remotely from the patient support by an authorized healthcare person. The authorization signal may be generated at the user interface 56b or remotely, such as by a handheld portable device (126) or a computer at the nurse call station or another remote device. Alternately, the prescription may be issued by a computer—either controller 52 or a remote computer by way of the hospital network, for example. This may be based on using predictive analytics or other parameters considered by the computer. In one embodiment, the features include the side rails, the Fowler section, a bed lift mechanism, and a patient support deck. For example, the prescription may be to prohibit the Fowler section angle from being less than 30 degrees. Another example includes a prescription to prohibit the bed lift mechanism from raising the deck above a certain height above the floor, for example no greater than 18 inches. In yet another example, the prescription prohibits the side rails from being lowered unless a healthcare person is adjacent the apparatus. Another example of a feature that may be selected and then purchased or prescribed is a hands-free bed movement software, such as described in U.S. patent Ser. No. 13/242/022, filed Sep. 23, 2011, by Richard Derenne et al. and entitled Video Monitoring System (P267A), commonly owned by Stryker Corp. of Kalamazoo, Mich., the complete disclosure of which is hereby incorporated herein by reference. For example, a hands-free bed movement software may be prescribed for a patient with a weakened immune system or may be purchased by a patient who has a heightened concern for infection.

Figure 4:
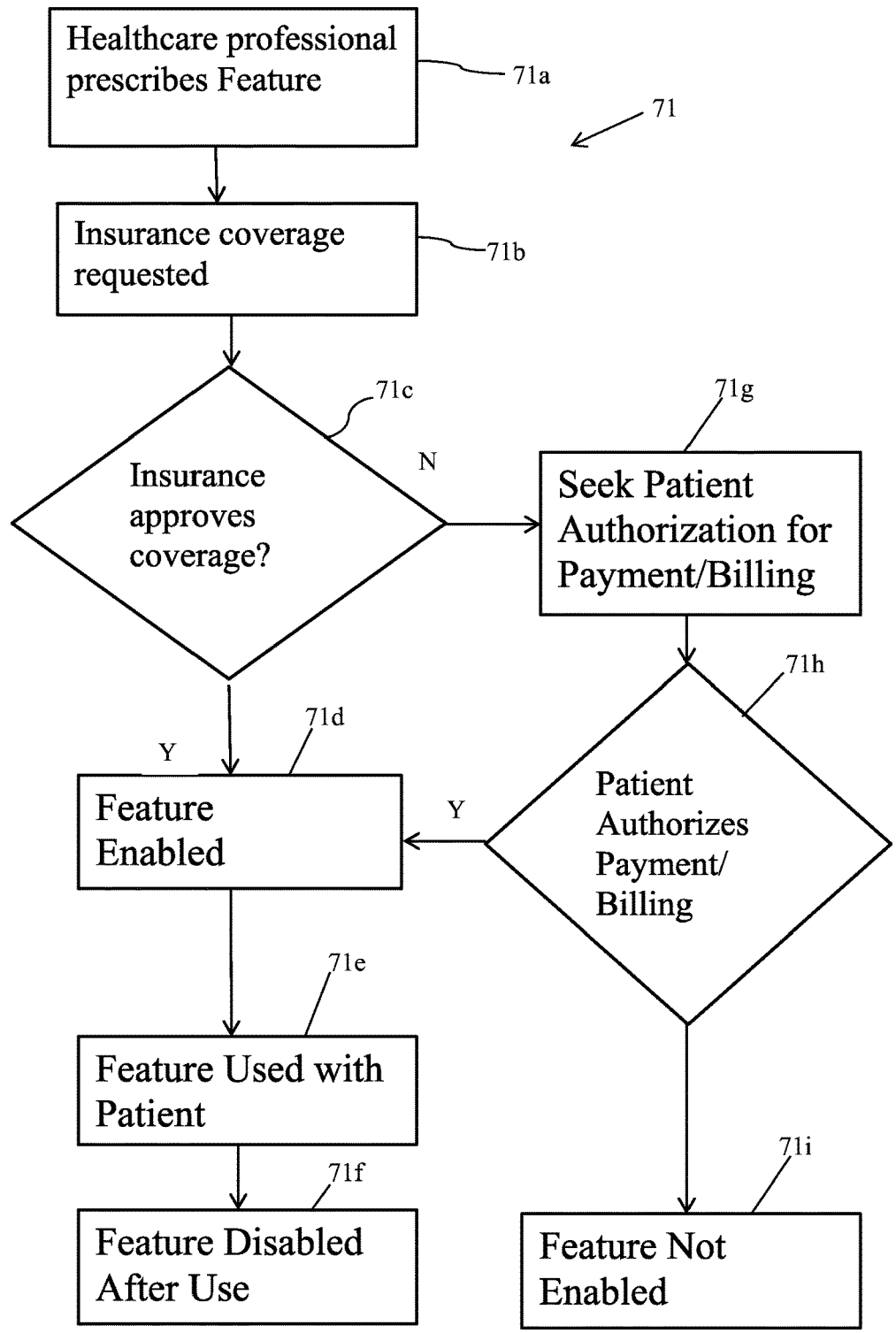
FIG. 4 is a flowchart of another embodiment of an authorization system that may be used to enable use of applications at the medical apparatus.

As illustrated in FIG. 4, controller 52 has another embodiment of a software authorization algorithm 71, which is based on a prescription authorization. The software begins at step 71a with an authorized user, such as an authorized healthcare person, prescribing the use of a feature using, for example, the caregiver user interface device 56b. The caregiver user interface may have a menu for selecting a feature and an additional control which when selected indicates that the selection is prescribed. In response to the prescription, the software then requests an insurance coverage inquiry at step 71b. If insurance coverage is approved, then the feature is enabled at step 71d. After the feature has been used on the patient at step 71e (for example, for a set period of time or number of prescribed uses) the controller then at step 71f disables the feature. If the insurance was not approved, the software will prompt the patient for authorization for payment or billing the patient at step 71g. Alternately, preapproval for use of various devices at the patient support may be obtained, for example, during the admission process. If the patient authorizes payment at step 71h, the software will proceed to enabling the feature at step 71d and follow through steps 71e and 71f. Optionally, the software at step 71i will not enable the feature if the patient does not authorize payment. As described above, the authorization may be issued by the computer using predictive analytics.

Optionally, patient support 10 is in communication with one or more networks. For example, as shown in FIG. 2, apparatus 10 may include a transceiver 60 that may be used by controller 52 for forwarding selected information from control system 50 to other devices, such as a healthcare facility computer network 72 (FIG. 5), or another recipient. Healthcare facility computer network 72 is often, though not necessarily always, an Ethernet, and it will be understood that computer network 72 can take on other forms. In one embodiment, transceiver 60 is a WiFi radio transmitter and receiver that are capable of communicating with a wireless access point of the hospital network 72 in accordance with IEEE 802.11 standards, or in accordance with other standards. More specific uses of transceiver are discussed below.

It will be understood by those skilled in the art that use of the term "transceiver" throughout this specification is not intended to be limited to devices in which a transmitter and receiver are necessarily within the same housing, or share some circuitry. Instead, the term "transceiver" is used broadly herein to refer to both structures in which circuitry is shared between the transmitter and receiver, and transmitter-receivers in which the transmitter and receiver do not share circuitry and/or a common housing. Thus, the term "transceiver" refers to any device having a transmitter component and a receiver component, regardless of whether the two components are a common entity, separate entities, or have some overlap in their structures.

In one embodiment, one or more software applications, such as billing or monitoring applications, may be provided at support apparatus 10 (as thin client, fat client, or local applications) that record the amount of usage of the features on or near or associated with the patient support apparatus 10, which are used with a particular patient. This information is forwarded by the application to the corresponding network service 76 where it is made available to the healthcare administrators who can use it to bill patients based on the amount of time and/or usage by the patient of the individual features of patient support apparatus 10 or use the information to assess the efficacy of a treatment, for example, for a given patient or in general.

In one embodiment, the billing or monitoring may be based on an association between the patient support and the feature. As described above, control system 50 may include a near field communications transceiver that communicates in any of the manners, and with any of the devices, disclosed in commonly assigned U.S. patent application Ser. No. 13/802,992, filed Mar. 14, 2013 by applicants Michael Hayes et al, and entitled COMMUNICATION SYSTEMS FOR PATIENT SUPPORT APPARATUSES, the complete disclosure of which is hereby incorporated herein by reference. The near field communications transceiver can then be used for establishing an association between patient support apparatus 10 and the feature, typically when the feature is not a bed-based feature. Such association information is forwarded to controller 52, which can then track the association for billing or monitoring purposes.

In addition to enabling the use of a feature, as noted, controller 52 may also be configured to track the use of a feature. For example the use of the feature may be monitored or tracked for insurance purposes, for compliance purposes, for diagnostic purposes, for trend analyses, including for future product development or modifications or for maintenance purposes. The use may also be tracked for monitoring patient activity, the efficacy of a therapy and/or device performance, for example. The forwarded information may include the associations with, and/or identifications of, the feature and the patient identification (ID). For example the information may be forwarded to electronic records system, such as an electronic medical records (EMR) system or forwarded to a third party. In the case of a feature that is a treatment device, as noted, the information may also be used to provide feedback either to alter treatment or halt treatment, or for diagnostic or software development purposes.

Controller 52 may be configured to create a software environment in which one or more thin client applications 78 are able to operate. Such thin client applications 78 communicate with one or more network services 76, 76a, 76b, etc. (FIG. 5), which are available on one or more remote networks, such as healthcare facility network 72 and/or the Internet 74. Controller 52 is therefore able to support one or more thin client applications 78 where a substantial portion of the computational workload carried out by the application is done remotely via one or more network services 76. The term "thin client" as used herein shall be given its ordinary and accustomed meaning in the field of computer science and software. In general, a thin client refers to a computer or computer program that depends substantially on another computer or, in this case, one or more network services 76, to fulfill its programmed computational functions. In some embodiments, controller 52 may be configured to support both fat and thin client applications, as well as applications that are purely local.

The thin client, fat client, and/or local applications may be used to enable the use of the various features described above, the billing associated with the use of the feature, the detecting and/or tracking of the associations, and/or the tracking or monitoring the use of the feature. The thin client, fat client, and/or local applications may operate via controller 52 to include other functionality, such as one or more of the following: patient assessment applications (e.g. assessing a patient's risk of falls, assessing a patient's risk of bed sores, etc.); sensor monitoring and/or data collection applications (e.g. gathering load cells outputs—such as patient position, center of gravity, weight, weight distribution, patient movement, etc.—gathering pressure mat outputs, gathering vital sign readings, gathering data from medical devices associated with support apparatus 10 and/or the patient assigned to the support apparatus 10); maintenance monitoring/scheduling applications (e.g. monitoring the actual usage of various components on support apparatus 10 for maintenance purposes); other billing applications (e.g. patient usage of support apparatus 10 and/or features at or near patient support apparatus 10); and/or patient care protocol management applications (e.g. defining, implementing, and/or monitoring of patient care protocols, such as protocols for preventing patient falls, protocols for preventing bed sores, protocols for turning patients, protocols for preventing ventilator-associated-pneumonia (VAP), protocols for containing or reducing infections, etc.).

Referring again to FIG. 5, patient support 10 may form part of a patient support apparatus software infrastructure layout or configuration 80 in a healthcare facility 84. Configuration 80 includes one or more patient support apparatuses 10 that have one or more thin client applications 78 operable thereon. The thin client applications 78 are in electrical communication with one or more network services 76 that are supported on a remote network. The remote network refers to one or more healthcare facility networks 72 positioned within a healthcare facility 84, or one or more networks positioned outside the healthcare facility 84, such as, but not limited to, the Internet 74. It will be understood by those skilled in the art that the term "healthcare facility"

will refer not only to an individual building in which patient support apparatuses 10 are positioned, but also collections of buildings (such as are commonly found on a hospital campus). Still further, it will be understood that healthcare facility network 72 refers not only to a Local Area Network that is positioned within a single healthcare facility 84, but also Wide Area Networks that may connect together multiple healthcare facilities 84 that are located in different geographical areas.

Thin client application 78 communicates with the remote network 72 by way of a communications link 82. Communications link 82, in one embodiment, is a wireless communications link that links together transceiver 60 with a wireless access point 88 of the healthcare facility network 72. In one embodiment, communications link 82 is a WiFi communications link and healthcare facility network is an Ethernet. In other embodiments, communications link 82 may be a wired communications link between transceiver 60 and healthcare network 72. Such a wired connection may be carried out by an Ethernet cable, a serial cable, or by other cables. In still other embodiments, communications link 82 is a wireless link that, in some instances, is carried out through the use of one or more mesh networks that patient support apparatuses 10 are part of. Such use of mesh networks to communicate information from patient support apparatuses 10 to a healthcare network, such as network 72, are disclosed in commonly assigned U.S. patent application Ser. No. 13/802,855 filed Mar. 14, 2013 by applicants Michael Hayes et al. and entitled PATIENT SUPPORT APPARATUS COMMUNICATION SYSTEMS, and commonly assigned U.S. Pat. No. 8,461,982 issued to Becker et al. and entitled COMMUNICATION SYSTEM FOR PATIENT HANDLING DEVICES, the complete disclosures of both of which are hereby incorporated herein in their entirety by reference.

Patient support apparatus 10 may also run a thin client application 78 that is dependent upon a network service 76 for carrying out one or more of its full functionality. As was described above, the specific thin client application(s) 78 can vary, and include, but are not limited to, enabling the use of one or more features at the bed based on local or remote authorization as well as billing applications and/or prescription applications that are needed for the controller to enable the feature. Other applications include the tracking, monitoring and/or data collection applications, maintenance monitoring/scheduling applications, patient care protocol management applications, and other applications that relate to patient support apparatus 10, or the features and other devices in communication with patient support apparatus 10. For more details of suitable thin client applications 78 and fat client applications 92 and a suitable communication layout reference is made to U.S. patent application Ser. No. 14/211,613, entitled PATIENT SUPPORT APPARATUS WITH REMOTE COMMUNICATIONS, filed on Mar. 14, 2014 (P414B), which is incorporated by reference herein in its entirety.

Figure 6:
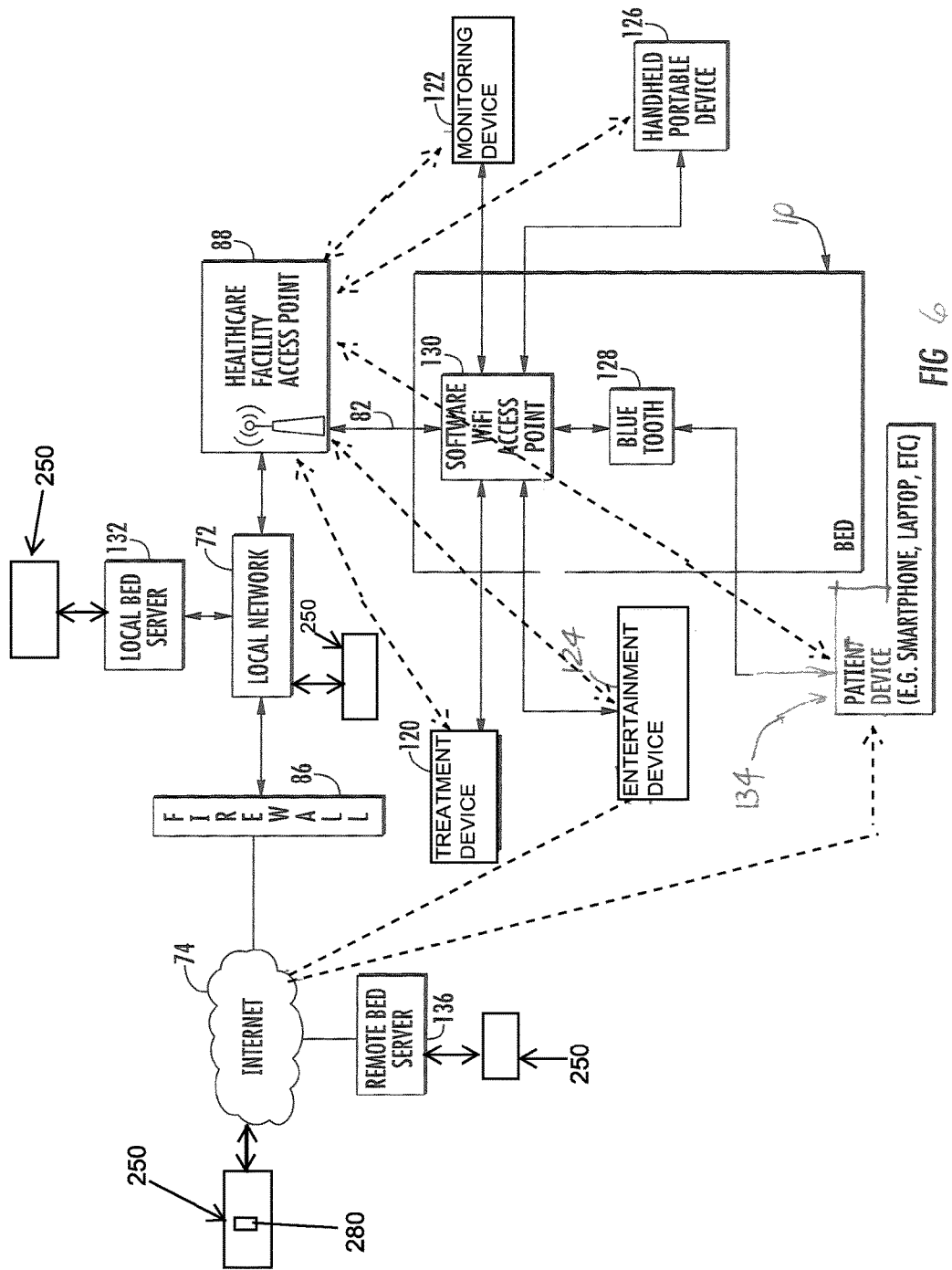
FIG. 6 is a schematic diagram of a medical apparatus communication system.
Figure 7:
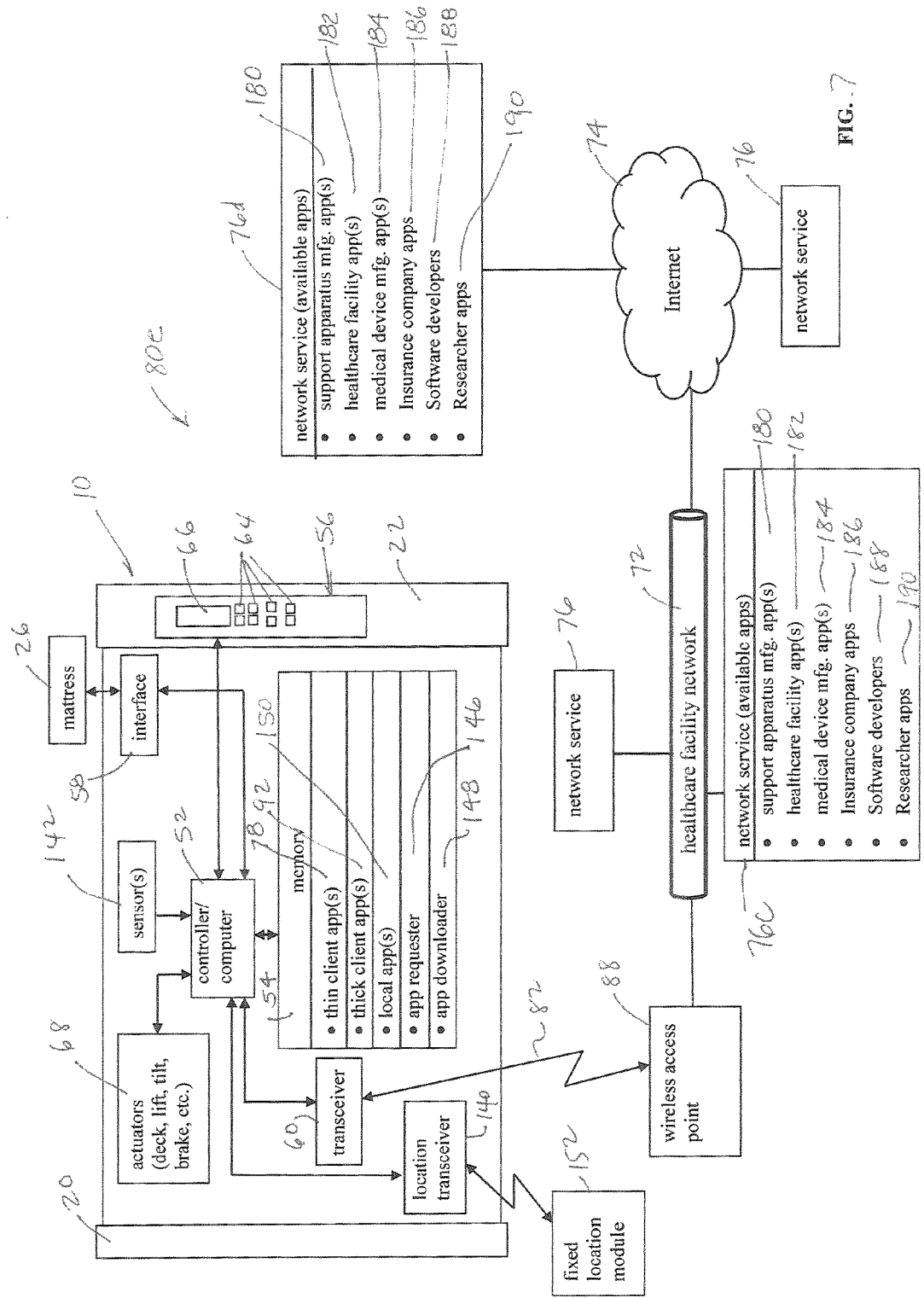
FIG. 7 is a schematic diagram of another embodiment of a medical apparatus communication system.

Referring to FIGS. 6 and 7, patient support apparatus 10 may include a control system that allows for patient support applications (apps) to be downloaded thereto. In one embodiment, patient support apparatus 10 may include purely local software 150 that controls the functions of patient support apparatus. In other embodiments, patient support apparatus 10 may have the ability to support thin client 78, fat client 92, and/or local applications, as described above. Referring to FIG. 6, patient support apparatus 10 may also include electronic circuitry and programming that create a software wireless access point 130. Access point 130 may comprise a separate module, which may be in communication with control system 50 via a wired or wireless connection, such as through a bed network, or not, or may be formed as part of control system 50.

Figure 5:
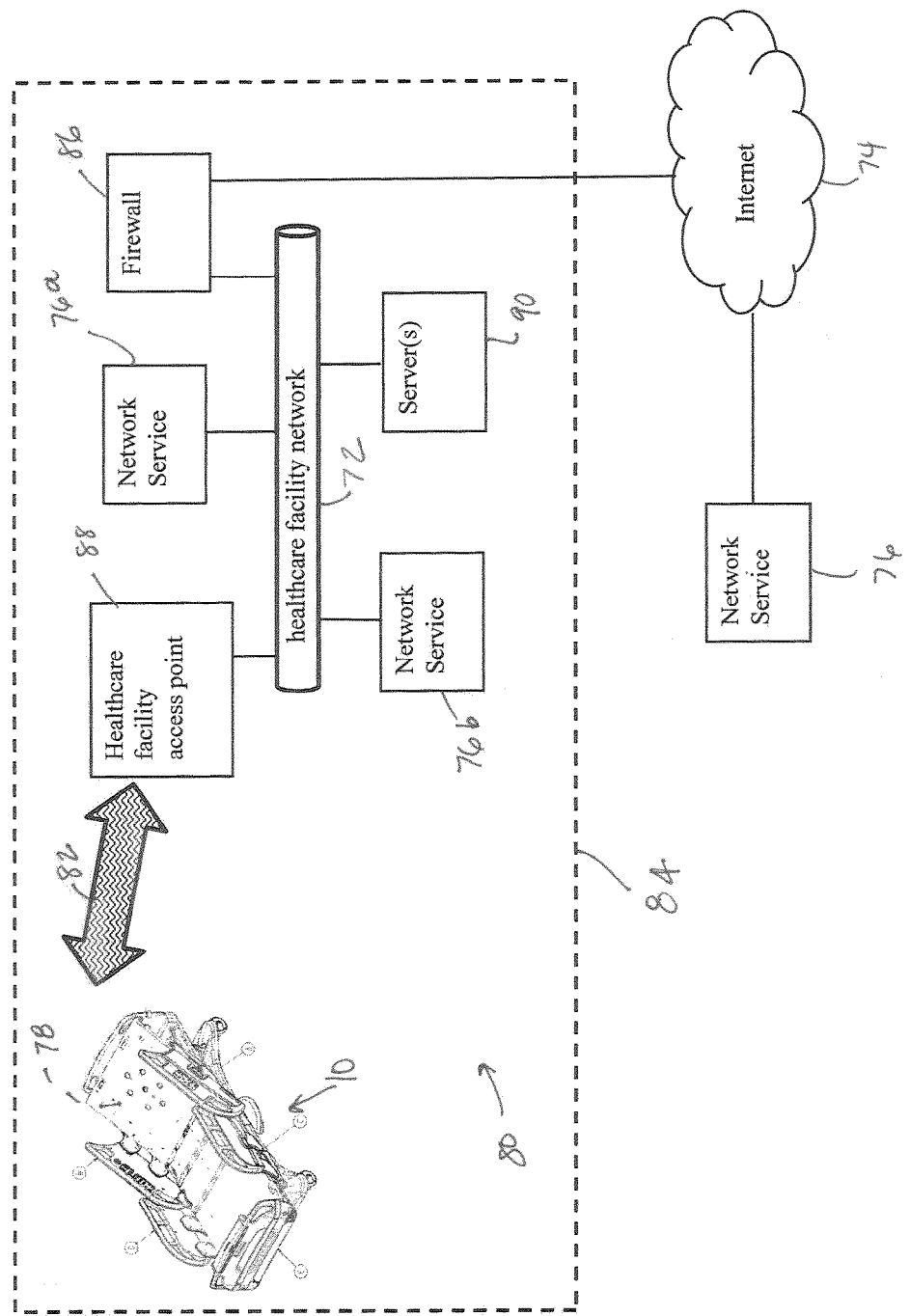
FIG. 5 is a schematic diagram of a medical apparatus and hospital communication system.

Software wireless access point 130 is connected by a wireless WiFi connection to any one or more of the wireless access points 88 within the corresponding healthcare facility (84, see FIG. 5). Wireless access point 88 is, as described above, electrically coupled to healthcare communications network 72, and, in some cases, the Internet 74 and any network services 76 that are hosted outside the healthcare facility, as well as—in the illustrated embodiment, a remote bed server 136.

Software wireless access point 130 provides a mechanism for any of a variety of different devices to communicate with network 72, including any servers that are installed thereon by the healthcare facility, as well as with the Internet 74, and resources or servers in communication with the Internet 74. In the embodiment shown in FIG. 6, a local bed server 132 is shown configured on the local network 72, while a remote bed server 136 is shown configured for Internet communications. In some embodiments, one or both of these servers 132 and/or 136 may be omitted. When included, local bed server 132 functions to receive data transmitted by patient support apparatus 10 (which is a bed in this example, although it will be understood that it could be any other type of medical apparatus) and make such data available to any other applications or servers running on the healthcare network 72, such as the information monitored by controller 52.

Local bed server 132 is also configured to communicate and receive data from any other applications or servers (e.g. servers 90, shown in FIG. 5) running on the healthcare network 72 and to forward such data to one or more patient support apparatuses 10 that are positioned within the healthcare facility. Such information includes, for example, patient information, patient room information, healthcare worker assignment information (e.g. which worker(s) are assigned to which patient(s)), and other information. Remote bed server 136 is capable of performing a variety of different functions, including gathering data from controller 52 on the use of an enabled feature as well as from sensors on board patient support apparatus 10, and is accessible through the Internet.

Software wireless access point 130 allows the patient support apparatus 10 to act as a local WiFi hotspot. Various devices having WiFi capabilities can connect to the access point 130 without having to undergo all of the healthcare facility's security, setup, and initialization procedures. In one embodiment, the WiFi hotspot may also be enabled as a feature (after receiving authorization) at the patient support in a manner described above. This allows a user to use the wireless access point 130 and tether their device or devices to the wireless hotspot, enabling them to communicate with network 72 and/or the Internet 74 after agreeing to payment or billing. Further, the manufacturer of the patient support apparatus 10 can configure access point 130 to control the manner in which devices are granted access to access point 130.

Examples of some of the various types of features, in the form of devices, that may communicate with a software WiFi access point 130 include, as shown in FIG. 6, a treatment device 120, a patient monitoring device 122, an entertainment device (such as a TV) 124, and a handheld portable device 126 (which may be a smart phone, computer tablet, personal digital assistant, portable computer, or other device). Patient support apparatus 10 also includes a second transceiver 128, which in the illustrated embodiment is a Bluetooth transceiver that is in electrical communication with access point 130. Second transceiver 128 enables features, in the form of devices, to access point 130 using protocols different from the protocol of access point 130. As shown, a plurality of one or more patient personal devices 134 (e.g. smart phone, laptops, PDAs, etc.) may connect to WiFi access point 130 using their Bluetooth connection, instead of their WiFi connection. Alternatively, such devices can connect to access point 130 using a WiFi connection (if available).

Referring to FIG. 7, memory 54 of controller 52 may have stored therein an application requester (app requester) 146 software used by controller 52 to request downloading software applications when a feature is selected but the feature is not resident on the patient support apparatus. For example, the patient support apparatus 10 may have hardware that is disabled and may not have any resident software that is suitable for use with the hardware. In another example, a non-resident device may be coupled to apparatus 10 for which apparatus 10 has no resident software that is suitable for use with the device. In yet another example, apparatus 10 may have resident software for which there is an upgrade available.

Therefore, when a software application is needed or requested to enable the use of hardware or a device, controller 52 (after being authorized) uses app requester 146 to communicate with an "available apps" network service 76c that includes a copy of the software application that is to be downloaded. As shown in FIG. 7, controller 52 uses app requester 146 to communicate a wireless request for the desired software application via communication with one or more wireless access points 88 of the healthcare facility network 72. The request may be to an "available apps" network service 76c that is local to the healthcare facility network 72, or it may be to an "available apps" network service 76d that is located on another network which is in communication with local network 72, such as a network connected to network 72 via the Internet 74. Regardless of the physical location of the "available apps" network service 76c or 76d, the "available apps" network service 76 is configured to transmit the appropriate software application that corresponds to the requested feature. The downloading of this corresponding software application is handled on the patient support apparatus 10 side by way of app downloader 148.

Once the appropriate software application is downloaded into memory 54 of patient support apparatus 10, controller 52—or an appropriate portion thereof—can enable the use of the downloaded software. After the software is enabled and its execution terminates, controller 52 may automatically delete it from memory 54, or it may automatically retain a copy of it, or it may decide whether to delete or retain a copy of it based upon the current amount of free memory available on board patient support apparatus 10.

Figure 8:
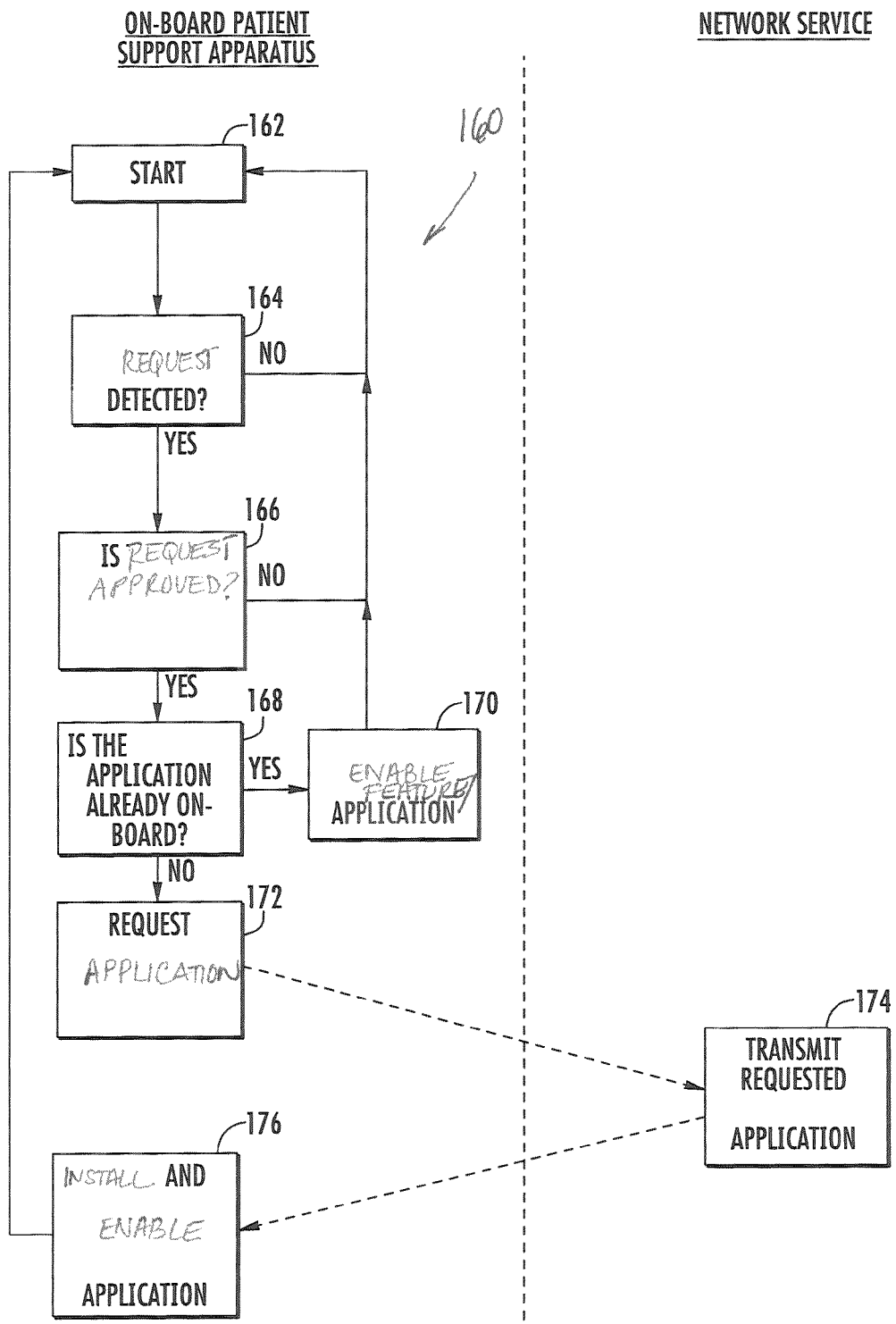
FIG. 8 is a flowchart of yet another embodiment of an authorization system when the feature is not onboard the medical apparatus.

Turning to FIG. 8, patient support apparatus 10 may include a software retrieval algorithm 160, which begins at an initial start step 162 followed by an evaluation step 164. Evaluation step 164 is carried out by controller 52 in response to detecting a request signal by a patient or a caregiver for a specific feature—in this case a feature that requires software that is not resident on the patient support to operate. If no request is detected, as determined in step 164, controller 52 returns to start step 162 and the algorithm 160 repeats itself. If, however, controller 52 determines at step 164 that a request signal is present, controller 52 proceeds to step 166 where it determines whether the request was authorized or approved. If the request has not been approved then controller 52 returns to start step 162.

If controller 52 determines at step 166 that the request has been approved, controller 52 proceeds to step 168 where it determines whether the corresponding software application for the requested feature is already stored on board patient support apparatus 10. Controller 52 performs this step by examining the contents of memory 54, or the contents of any other memory on board patient support apparatus 10 where such a software application might be stored. If controller 52 determines at step 168 that the corresponding software is already aboard patient support apparatus 10, it proceeds to step 170 where it begins to execute the on-board software to thereby enable the feature.

If controller 52 determines at step 168 that the corresponding software application is not on-board, it proceeds to step 172 where it requests a copy of the corresponding software from network service 76c and/or 76d. Request step 172 is carried out by sending one or more appropriate messages to healthcare facility network via transceiver 60 which, as described above, is a WiFi transceiver in some embodiments, or any other suitable transceiver can be used. The request sent at step 172 is conveyed by healthcare network 72 to network service 76c or 76d, which, at step 174 processes the request and begins transferring the requested software application. The particular software application that is transmitted by network service 76c or 76d is either stored in memory local to network 76c, 76d, or it is stored remotely and service 76c or 76d is configured to retrieve it from this remote location and transmit it to the requesting patient support apparatus 10. At step 176, controller 52 receives the transmitted software application and begins executing it, while thereafter returning to start step 162.

In one embodiment, a selected feature may include software used to control and/or communicate with a mattress 26 positioned on top of the patient support apparatus 10. In this example, the situation detected by one or more sensors 142 is the presence of a mattress 26 positioned on deck 18 of patient support apparatus 10. Such sensors may be near field sensors that communicate with a near field transmitter on the mattress 26, or they may be any of the other types of sensors described above.

In addition to merely detecting the presence of mattress 26, patient support apparatus 10 is also adapted to detect the type of mattress 26 positioned on deck 18. This type of detection may include a specific serial number, or product number, or it may include a more general model of mattress 26. By including this information, controller 52 is able to determine whether there are any software applications that correspond to this specific serial number, product number, or model of mattress 26. Patient support apparatus 10 is therefore able to download the appropriate software application for use to control and/or communicate with the specific type of mattress 26 positioned thereon as requested by the user. For example, the mattress on the patient support apparatus may have hardware features for which controller 52 has no software for controlling. Once that feature is requested for example by a caregiver or a user, then controller 52 may request the required software to be uploaded to the patient support so that the request can be fulfilled. Also, if the mattress 26 is later changed to a different model or type that has different functionalities, or a different communication interface, controller 52 may be configured to automatically detect this new type of mattress 26 and obtain, via network service 76c or 76d, the corresponding software application that pertains to that specific type of mattress or obtain it after receiving a request from a caregiver or user.

By designing patient support apparatus 10 so that it is not constrained to work with only one type of mattress, or a limited number of mattresses, but instead is able to dynamically obtain any corresponding mattress software applications, patient support apparatus 10 allows hospitals to not only use a variety of different mattresses 26 with a given patient support apparatus 10 without losing any functionality, but also allows the software used to control the patient support apparatus 10 to be updated so as to enable the hospitals or user to select use of the latest improvements, features, and modifications to the mattresses 26 and the control and/or communication with the mattresses 26.

The mattress software application(s) that is downloaded via app downloader 148, in conjunction with "available app" network service 76c or 76d, may utilize the existing hardware present on patient support apparatus 10, as well as the hardware contained with the mattress 26 to carry out this control/communication. Thus, for example, the downloaded software application will interact with the mattress 26 via interface 58. Further, the downloaded software application will likely also communicate with user interface 56 on the footboard 22 of patient support apparatus 10. Such communication may include the displaying of one or more icons, controls, or other information on display 66 of user interface 56, as well as the monitoring of, and reaction to, the pressing of one or more buttons 64. The downloaded software application, in some embodiments, will take over the control of all or a portion of screen space on display 66, at least for certain amounts of time. The software application may also display on display 66 any or all of the features that can be selected to be controlled on the mattress 26, as well as the means for exercising control over those features, and requesting means for selecting one or more of the features.

Such features may include inflating the mattress, deflating the mattress, redistributing patient interface pressure over the mattress, setting levels of patient immersion into the mattress, performing therapy on the patient using the mattress (such as percussion therapy), assisting in patient turning by inflating one or more side bladders, and performing still other functions. By utilizing the existing user interface 56 on patient support apparatus 10, it is not necessary for the mattress 26 to include its own user interface, but instead can rely upon the user interface already incorporated into patient support apparatus 10.

In another embodiment, patient support apparatus 10 may have built-in sensors that detect when a patient has, or is about to, exit from the patient support apparatus, but which are not presently enabled for use with the controller. Such sensors may include air pressure sensors, pressure sensors, or other conventional sensors. Again, a user or caregiver may wish to select the additional functionality that can be provided by the sensors by requesting controller 52 to download software for enhancing or enabling the functionality of the sensors. For example, when a user selects and authorizes controller 52 to obtain a bed exit software, controller 52 can issue the software to generate an alarm when the patient has exited, or is about to exit. In other words, controller 52—under the control of the downloaded software application—can use the existing audio or visual hardware on board patient support apparatus 10 to provide an alarm indication when the patient has exited, or is about to exit, from the patient support apparatus 10, as detected by the sensors. Such hardware may include one or more beepers, speakers, lights, or the like. Still further, controller 52 may send a signal to a nurse call system coupled to the patient support apparatus, and/or it may send a signal via transceiver 60 to one or more servers in communication with the healthcare facility network 72.

When a patient support apparatus 10 is equipped with patient exit detection capable sensors, such as load cells, it allows a patient support apparatus 10 that does not have patient exit detection capability by itself to be easily converted to a patient support with such exit detection capability through the simple addition of an appropriate software upon a request and authorization as describe above. Further, as advances and/or changes are made to the exit detection algorithms and/or sensors, these can be automatically incorporated into the patient support apparatus 10 by way of an automatic update or by request from the caregiver or user.

One illustrative type of mattress 26 that may be used with patient support apparatus 10 and controlled, either partially or wholly, via software running on controller 52, includes any of the mattress embodiments disclosed in U.S. patent Ser. Nos. 13/836,813; 14/019,353; and 14/308,131, entitled INFLATABLE MATTRESS AND CONTROL METHODS, PATIENT SUPPORT COVER, and PATIENT SUPPORT COVER, respectively, filed on Mar. 15, 2013; Sep. 5, 2013, and Jun. 18, 2014, respectively, all commonly owned by Stryker Corp. of Kalamazoo, Mich., the complete disclosures of both of which are hereby incorporated herein in their entirety by reference. It will be understood by those skilled in the art, however, that other types of mattresses may be used with patient support apparatus 10.

In another embodiment, another feature that may be requested and then prescribed (e.g. by an authorized healthcare person) may be a ventilator, which is not resident on the patient support apparatus. For example, a ventilator protocol application may be provided and available for upload to controller 52 for use at the patient support and allow the ventilator and its protocol application to be requested and authorized for use at the patient support apparatus, as described above. Further, the protocol application may include a customization interface. This customization interface allows the ventilator protocol to be modified in accordance by caregiver or authorized healthcare administrators. Such customization allows the caregiver or administrator to, for example, set the minimum threshold angle of the Fowler section of the patient support apparatus which is not to be broken during the implementation of the ventilator protocol. Other customizations are also possible.

As another example, the feature may comprise a compliance application for use in monitoring compliance with one or more patient care protocols. For example, one protocol may require that the Fowler portion of a bed (e.g. head section 28 of patient support apparatus 10) be maintained at an angle above a specified threshold. When carrying out the compliance application, controller 52 communicates with a sensor (not shown) that measures the angle of the Fowler portion on patient support apparatus 10 and records the outputs from this sensor and forwards them to a compliance network service.

One or more maintenance applications may also be requested (e.g. by the caregiver) to operate on patient support apparatus 10 as thin client, fat client, and/or local applications. In one embodiment, a maintenance application operates on patient support apparatus 10 that counts the number of times each of the various actuators 68 on board patient support apparatus 10 are used. This may be particularly useful to a manufacturer who can receive data from the hospital about its equipment through a network service 76. These actuators include the tilt actuator 68a, deck actuator(s) 68b, lift actuator(s) 68c, and/or brake actuator(s) 68d. The maintenance application may record the counts for each of the individual actuators and compare these counts to thresholds corresponding to each of these various actuators. If any of the counts exceed the corresponding threshold, a maintenance alert is issued (either locally, remotely, or both) by the maintenance application. Preventative maintenance can then be performed on the patient support apparatus based upon the device's actual usage, rather than a simple passage of time (which may or may not reflect use conditions). The maintenance application therefore helps ensure that patient support apparatuses 10 receive the proper care in a timely manner. This application may be purchased, therefore, by the hospital.

In addition to counting the physical movement of various components of patient support apparatus 10, the maintenance application can also keep track of the number of times one or more rechargeable batteries on the patient support apparatus 10 are charged and discharged. Further, the extent of the discharging and recharging can be monitored and recorded. This information is then transmitted to network service 76 which uses the information to determine when the rechargeable batteries should be replaced. This helps to ensure that the rechargeable batteries are replaced on a timely basis, but not unnecessarily often.

Another type of application that can also, or alternatively, operate on patient support apparatus 10 as a thin client, fat client, and/or local application is a data-gathering and analysis application. The data gathering refers to the gathering of any sensor information that the patient support apparatus is capable of generating about the patient, which may be useful to the hospital or third parties, such as insurance companies. These applications may also be downloaded to memory 54 using the app requestor software 146 and app down loader software 148. For example, applications, such as insurance company applications 186, software developer applications 188, or researcher applications 190, may be downloaded into memory 54 for use by controller 52 to collect data relative to the use of the patient support, patient care, patient environment, and patient health, including patient activity.

The information can then be forwarded by the application to a network service 76 (whether inside firewall 86 or outside firewall 86) that stores the data to allow studies on the data. The types of studies are customizable according to the interests of the third party of the patient support apparatus 10, or according to the interests of one or more healthcare facilities. Such studies might include, for example: Predictive analytics that look for: correlations between patient movement on support surface 28 (as measured by force sensors 68) and the subsequent exiting of the patient from the patient support apparatus 10; evaluations of risk factors to prevent readmission; sleep studies; studies for sleep apnea; other patient safety studies (e.g. reviewing turning schedules, patient activity, or patient activity for decubitus care). Such studies may be capable of finding patterns and correlations between certain movements and the subsequent exiting of a patient from the support surface 28. By finding such patterns for a particular patient, it will be possible to adjust an exit alert system application so it can issue exit alerts of the patient's exit sooner than standard alert systems. By issuing such alerts further in advance of patient exit, a caregiver is given more time to come to the room the patient is in and assist him or her in exiting from the support apparatus 10, thereby reducing the risk of a patient fall. Studies may include monitoring of how the patient support or devices operate for software development purposes. Other studies may include housekeeping studies or infection control studies. Other types of studies may also be carried out using such data gathering applications.

Any of the foregoing applications that can operate on patient support apparatus 10 may also include a customization interface feature. Such a customization feature allows healthcare institutions to modify the corresponding application to meet their particular needs. Such customization gives the healthcare facility greater flexibility in billing, maintenance, patient care, data collection, and compliance monitoring.

Consequently, as described above, control system 50 may be adapted to support patient support apps that provide new features on the patient support apparatus 10. For example, some patient support apparatuses 10 may be sold to customers with a patient scale system (e.g. a set of load cells 62 that are able to determine patient weight), but no patient exit detection system. If the user or caregiver or even the customer later desires to add a patient exit detection systems, the patient support app (after establishing proper authorization) can be download that utilizes the existing scale system to implement a patient exit detection system. For example, the patient exit detection system app can utilize the outputs of the load cells 62 to calculate the center of gravity of a patient positioned on the patient support surface 28 and issue an alert if the patient's center of gravity moves outside of a selected zone. One manner in which these center of gravity and alerting functions may be carried out is disclosed in commonly assigned U.S. Pat. No. 5,276,432 issued to Travis and entitled PATIENT EXIT DETECTION MECHANISM FOR HOSPITAL BED, the complete disclosure of which is also hereby incorporated herein by reference.

Still another type of software application that is downloadable by patient support apparatus 10 using app requester 146 and app downloader 148 is one that enables patient support apparatus 10 to communicate with a nearby medical device. The medical device may be any of a variety of different types of medical devices that are positioned within the vicinity of patient support apparatus 10, such as, but not limited to, pumps, ventilators, monitors, vital signs sensors, etc. Patient support apparatus may include sensors 142 (FIGS. 2 and 7) that detect the presence of the nearby medical device and the type of medical device. Such type of information may include not only information indicative of whether the medical device is a pump, monitor, ventilator, vital sign sensor, etc., but also the manufacturer information and/or specific model of the medical device. This information may be included in the message sent out by app requester 146 to the "available apps" network service 76c, 76d so that the network service 76c, 76d can locate the necessary software application that enables communication with that specific type of medical device. Once a user or caregiver requests a device to be enabled (after authorization), controller 52 downloads the software that is appropriate for using the device and executes it so that it is able to communicate and enable use of the medical device and receive and/or transmit patient information to or from it. By having this software application downloadable from the network service 76c, 76d, the patient support apparatus 10 can be configured to communicate with new medical devices that may use different communication protocols, or that are capable of conveying different types of data than other types of medical devices.

Another type of software application that is downloadable by patient support apparatus 10 using app requester 146 and app downloader 148 is one that is used for billing purposes. As described above, such a software application may monitor the length of time that a patient or caregiver uses a feature at or near or that is associated with the patient support apparatus 10. By keeping track of the amounts of time that such devices are used, or are otherwise associated with a particular patient, a healthcare facility can use that information to generate invoices that are more reflective of the actual amount of medical resources used by a particular patient. As also noted above, prepayment may be made or preapproval may be given either based on usage or a fixed time period. Such software applications may be updated periodically through network services 76c or 76d to reflect new billing criteria. Further, such software applications may be configured to automatically transmit their accumulated usage information to a remote server that uses such information to generate invoices and/or for the purpose of studying the use of a feature.

One type of software application that may be downloaded includes a patient support apparatus manufacturer application 180. Application 180 may comprise a software application that controls the communication between the patient support apparatus 10 and the mattress 26 positioned thereon. Another type of software application might be a software application that allows patient support apparatus 10 to communicate data directly with one or more other patient support apparatuses 10. Another type of software application may include a healthcare facility application 182, which can be used by caregivers to perform patient assessments (e.g. fall risk, bed sore risk, etc.) and/or to implement, monitor, or create patient care protocols. Another example of a software application includes a medical device manufacturer application 184 that allows the patient support apparatus 10 to communicate with a medical device positioned in the vicinity of the patient support apparatus 10, such as a pump, ventilator, vital signs sensor, temp sensor, or other patient sensor to gather data about the device and then optionally forward it to a third party, such as the manufacturer. Still other types of software applications are, of course, possible.

It will also be understood by those skilled in the art that, although FIG. 5 only depicts a single patient support apparatus 10, multiple patient support apparatuses 10 will typically be in communication with the various network services 76. All such patient support apparatuses 10 within the healthcare facility will therefore automatically be provided with the software applications that correspond to their specific situations.

In yet another embodiment, patient support apparatus 10 comprises a chair, such as a medical recliner or a chair in a waiting room. Apparatus 10 may include one or more sensors for sensing a physiological parameter of a patient. For example, the sensor or sensors may comprise a temperature sensor or a sensor that detects vital signs. Controller 52 receives the sensor signals and analyzes the signals (e.g. compares them to stored values in memory 54). When controller 52 determines that there is an alarm condition based on the sensor signals, controller 52 is adapted to send an alarm signal, for example, through transceiver 60 to the network 72 so that a healthcare person may be notified of the alarm condition of the patient supported on patient support 10. For example, the alarm may indicate to the healthcare person that the patient needs assistance and/or needs to be isolated.

When patient support apparatus 10 is implemented as a recliner, it may be a recliner such as that disclosed in U.S. patent application Ser. Nos. 14/212,417; 14/212,009; 14/212,323; and 14/212,253 (STR03D P-410A, 410B, 410C, 410D), filed Mar. 14, 2014, by applicant Richard Derenne and entitled MEDICAL SUPPORT APPARATUS, all commonly assigned to Stryker Corp. of Kalamazoo, Mich., the complete disclosure of which is incorporated herein by reference. Other types of recliners may, of course, be used.

In another embodiment, control system 50 of apparatus 10 is in communication with a remote store 250 (FIG. 6) that includes downloadable software applications 280 for use at the medical apparatus 10. Remote store 250 may be located on a central server on premise and accessible through a local network or on a local bed server or may be located off premise, for example, on a third party server and accessible through the internet or may be located in a Cloud service, or a combination of any of the above.

The control system 50 is configured to associate a patient with the medical apparatus 10 and to download from the remote store 250 a software application 280 for use at the apparatus 10 based on information about the patient.

Figure 9:
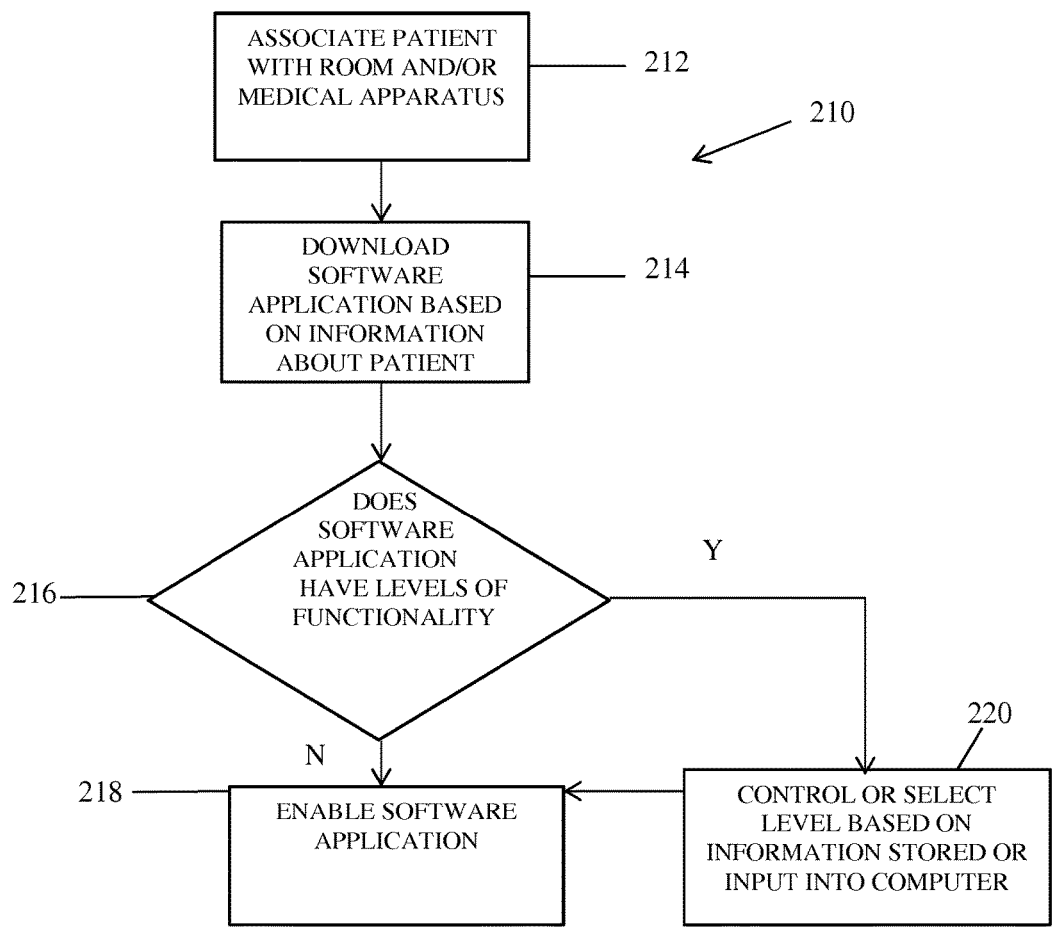
FIG. 9 a flowchart of yet another embodiment of a medical apparatus communication system.

Turning to FIG. 9, patient support apparatus 10 may include a software algorithm 210, which begins at an initial step 212 where control system 50 of apparatus 10 associates a patient with the room or medical apparatus 10. After the patient is associated with the room and/or apparatus 10, software 210 at step 214 downloads a software application or software applications based on information about the patient, which is retrieved or read, for example, from an EMR/EHR system or a hospital network or $3^{rd}$ party server.

At step 216, software algorithm 210 detects whether the downloaded software application or applications have levels of functionality. If the software application or software applications do not have any levels of functionality, software application 210 enables the use of the downloaded software application at step 218. If the downloaded software application or applications have levels of functionality, software 210 at step 220 controls or selects a level based on information about the patient or caregiver read by, retrieved by or input into the controller 52.

As described above, control system 50 may include a near field communications transceiver that can be used for establishing associations between apparatus 10 and other objects, such as patients or caregivers wearing near field tags with identifying information (ID) that identifies the patient or caregiver. The association is initially established by control system 50 receiving or reading the patient's or caregiver's ID based on the signal from the near filed ID tag. Control system 50 then communicates with an electronic records system, for example, an EMR system, an EHR system, an ADT system, or the hospital network, to read or retrieve information about the patient or caregiver based on the ID. Reference is made again to commonly assigned U.S. patent application Ser. No. 13/802,992, filed Mar. 14, 2013 by applicants Michael Hayes et al, and entitled COMMUNICATION SYSTEMS FOR PATIENT SUPPORT APPARATUSES, the complete disclosure of which is hereby incorporated herein by reference.

In one embodiment, once the association is made between a patient and apparatus 10 and memory 54 includes stored therein information about the patient, control system 50 evaluates the information and determines whether a software application or applications are needed to care for the patient. Once control system 50 determines a software application is needed in the care of the patient, control system 50 will download the software application 280 from remote store 250.

The software applications 280 may be health-based applications, e.g. related to monitoring the vital signs of a patient, relating to fall prevention, displaying of EMR/EHR information, displaying an X-ray image, or may be entertainment based applications, e.g. playing of music, playing of videos or movies.

In some embodiments, the downloaded application may have levels of functionality. Further, in one embodiment the control system 50 is configured to control or select which level of the application is going to be used or be available at apparatus 10 based on information input to or stored in the memory 54, such as a user's credentials. For example, the user's credentials may be input by the user or detected or determined by the computer (e.g. read or retrieved or received from an electronics records system, based on the user's ID). As described above, the user may wear a near field tag, such as an RFID tag, which when detected by the control system identifies to the computer who the user is and/or their credentials. Further, as described above, an association may be initially established by control system 50 receiving or reading the user's ID based on the signal from a near field ID tag, such as an RFID tag. Control system 50 then communicates with an electronic records system, for example, an EMR system, EHR system, ADT system, or the hospital network, to read or retrieve information about the user based on the ID.

In another embodiment, the association between the patient and apparatus 10 may be based on input, either locally or remotely, into the computer via user interface 56 or a remote interface, such as at the hospital admissions department. For example, when a patient is assigned to a room and/or to a medical apparatus, such as when the patient is first admitted to the hospital, the electronics records system (such as an EMR/EHR system) will associate the patient with the room and/or apparatus 10. Apparatus 10 is then programmed to read or retrieve information about the patient from the EMR/EHR or another electronics records system and automatically download/install the application or applications needed for proper care of the patient once the patient is associated with the room or apparatus 10.

The download may be automatically done at the time the patient is first assigned to the room and/or to apparatus 10, or may be based on a status or change in status of the patient. For example, the status may be determined by periodically reading or receiving information about the patient, such as by reading or receiving information from one or more electronic records system, such as EMR/EHR system, reading or receiving information from other hospital systems, and/or by the output from another application(s).

In some embodiments, controller 52, which is in communication with user interface 56, allows a caregiver to input the association between the patient with the apparatus 10, for example, by inputting the patient ID into controller 52 via user interface 56. In one embodiment, control system 50 then retrieves or reads information about the patient based from one or more electronic records system, such as EMR/EHR system, based on the patient's ID. The user interface 56 generates and transmits an association signal to the computer in response to input at user interface 56, with the controller 52 then programmed to download the application in response to the association signal and the information retrieved from the electronic records system.

As described above, memory 54 of controller 52 may have stored therein an application requester (app requester) 146 software used by controller 52 to request downloading of one or more software applications 280 from store 250. Once the appropriate software application is downloaded into memory 54 of apparatus 10, controller 52 is programmed to enable the use of the downloaded software. After the software is enabled and its execution terminates, controller 52 may automatically delete it from memory 54, or it may retain a copy of it until the patient is no longer associated with the apparatus.

Turning again to FIG. 8, apparatus 10 may include a software retrieval algorithm 160. In this application, controller 52 skips to step 168 where it determines whether or not the application or applications needed for proper care of the patient are already on-board patient support apparatus 10. If so, it proceeds to step 170 where it begins to execute the on-board software.

If controller 52 determines at step 168 that the application (or applications) needed for proper care of the patient application is not on-board, it proceeds to step 172 where it requests a copy of the software application from remote store 250. Request step 172 is carried out by sending one or more appropriate messages to the healthcare facility network via transceiver 60 which, as described above, is a WiFi transceiver in some embodiments, or any other suitable transceiver can be used. The request sent at step 172 is conveyed by healthcare network 72 to store 250, which, at step 174 processes the request and begins transferring the requested software application. As described above, store 250 may be located locally on a local bed server or a central server or a remote server or in a Cloud service. At step 176, controller 52 receives the transmitted software application and then optionally generates a user interface device, such as an icon at display 66 that is configured to operate the application. The controller 52 optionally begins executing the software application (depending on whether it requires a user's input) or executes it when requested, for example, when requested by a user via the user interface device.

In one embodiment, as noted, controller 52 generates an icon at display 66 that represents the downloaded software application and which forms a user input device for a user to select the use of and control the software application. Optionally, controller 52 generates a menu in response to a user touching the icon to select the software application, which menu allows a user to control the downloaded software application.

Optionally, as described above the user interface 56 may be resident at apparatus 10 or may be a remote user interface remote from the apparatus and configured to communicate with the controller 52 either wirelessly or through a wired connection. For example, the remote user interface may communicate with the computer through a network.

Alternately, in one embodiment the association and/or information are input into controller 52 by way of a reader, such as a barcode reader. For example, where the patient wears a bar code (e.g. on a bracelet), which contains the patient ID and optionally patient information, the ID and information may be read by or transmitted to the reader and communicated to controller 52. Where the bar code simply transmits the patient ID, controller 52 is then programmed to read or retrieve the additional information about the patient from an electronics records system as described above.

Optionally, the controller 52 monitors the use of the downloaded application and generates a use information signal about the use of the feature. In a further aspect, the use information signal is communicated by the system 50 to a remote location. For example, the remote location may be a hospital network or may be a network of third party, including, for example, a Cloud service, where the use information may be stored and/or used for billing, evaluation, or documentation.

In one embodiment, apparatus 10 includes a store interface that allows a user to select an application for download to the medical apparatus. For example, display 66 may have an icon that represents store 250 and forms the store interface, with one or more user input devices, such as buttons or touch sensitive areas of the display 66, which then form a menu of applications from which the user may select for download. When an application is selected for download, control system 50 generates at display 66 one or more additional user input devices, such as buttons or touch sensitive areas of the display, which allow a user to access and further control the application once downloaded.

Optionally, the control system 50 or the store 250 interface may be configured to control the availability of the application based on a parameter—for example—a parameter of the end user. In one aspect, the parameter is the security level of the end user, for example, whether the end user is a patient, nurse, physician, or other caregiver. The parameter may be input into the controller 52 by a user or may be read or retrieved by control system 50 based on the user's ID, as described above. In another embodiment, the parameter may be the skill level or training of the user.

In some embodiments, as described above, the user interface may be a separate device from the apparatus 10, such as a phone, a watch, a tablet, a desktop or laptop computer, or a secondary medical device, which is securely connected to the apparatus 10. In this manner, input to control system 50 may be remote from apparatus 10. Alternatively, the user interface 56, including display 66, may be mirrored to another device, such as a phone, a watch, a tablet, a desktop or laptop computer, or a secondary medical device, so that display 66 can be viewed and controlled remotely on a remote device.

In yet another embodiment, control system 50 is programmed to configure, modify and/or limit the user interface 56 (and optionally user interfaces 56a, 56b) or functionality of the user interface or interfaces based on a condition. The condition may comprise a condition of a patient or staff or comprise a specific care condition or hospital protocol. The conditions, for example, include the type or acuity of the patient, level or type of experience or training of the user, level or type of experience or training of the caregiver, level or type of experience of the hospital, level or type of the facility protocols or specifications, etc.

Figure 10:
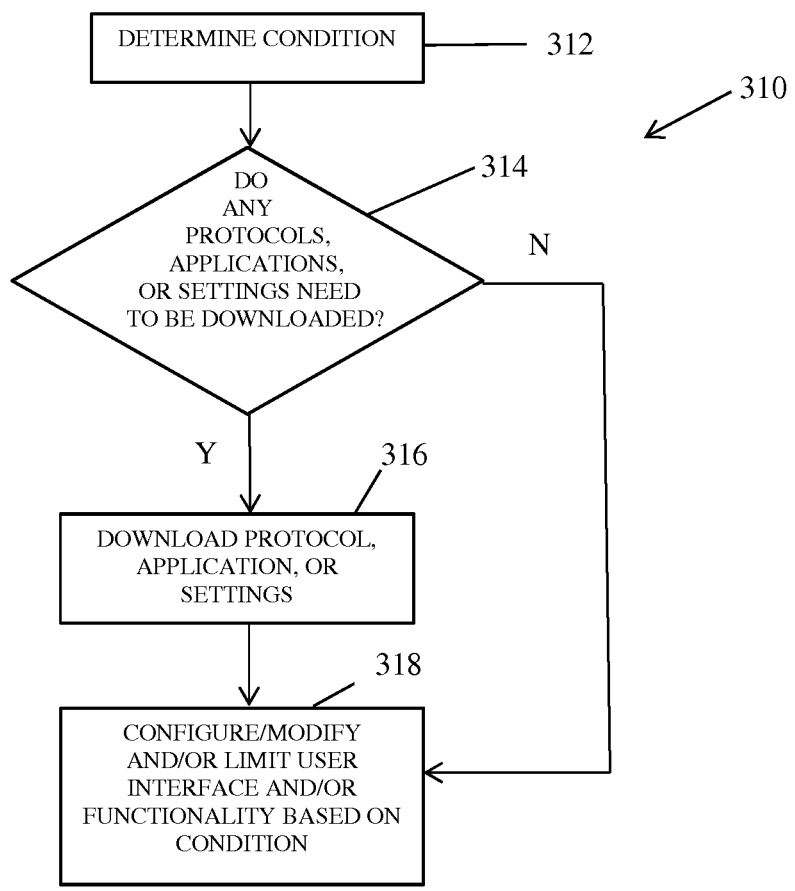
FIG. 10 is flowchart of yet another embodiment of a medical apparatus communication system.

Referring to FIG. 10, control system 50 may include a software application 310, which starts at step 312 where control system 50 determines a condition of a patient or caregiver. As will be more fully described below, control system 50 determines the condition of the patient or caregiver based on information that is read or retrieved from an electronic records system, such as an EMR/EHR system based on the association of the patient or caregiver with the apparatus 10.

Optionally, control system 50 at step 314 checks to see if any protocols or applications or settings need to be downloaded to care for the patient. If control system 50 determines at step 314 that no protocols, applications, or settings need to be downloaded, control system 50 at step 318 will configure, modify and/or limit the user interface of apparatus 10 and/or functionality of the user interface based on the condition.

If control system 50 at step 314 determines that a protocol, an application, and/or setting needs to be downloaded, control system 50 will download the protocol, application, and/or setting from a remote electronic system, such as a hospital network, a third-party server, or a Cloud service.

In one embodiment, the condition is input into controller 52 via the user interface 56. For example, control system 50 is programmed to allow a user to "log-in" to apparatus 10 and to associate the user or patient to the apparatus using a user or patient ID. Based on the association, control system 50 is programmed to then read or retrieve information about the user or patient from an electronics records system, for example, from EMR/EHR records, from a hospital network, which includes the condition. The control system is then programmed to configure the interface based on the condition.

In another embodiment, a user inputs at interface 56, or remotely via any of wireless devices described above, a condition of a patient into control system 50. Such conditions may include risk factors or conditions, such as described in U.S. Pat. No. 9,149,190 (P399B), which is commonly owned by Stryker Corporation of Kalamazoo, Mich. and hereby incorporated by reference in its entirety herein.

In one embodiment, apparatus 10 comprises a hospital bed. The control system 50 of the hospital bed is programmed to modify one or more user interfaces, e.g. user interface 56 (including display 66), 56a, and/or 56b, to limit certain functionality of one or more components of apparatus 10 based on the particular patient assigned to or based on the user operating apparatus 10.

When a patient is associated with that bed (as described above and the control system 50 has retrieved information about the patient's condition from an electronic records system) and has a condition where movement of a component of the bed could be detrimental to the patient, control system 50 is programmed to limit the ability of a user to move the component, for example, a side rail, the lift mechanism, the deck actuators, or the like. For example, when a patient is associated with a bed (as described above and the control system 50 has retrieved information about the patient's condition from an electronic records system) and has a condition where movement of a section of the deck could be detrimental to the patient, control system 50 is programmed to limit the ability of a user to alter the angle or limits the range of permissible angles of the deck section of the bed, e.g., the angle of the head (the "HOB") or foot section of the bed. Control system 50 is programmed to limit the functionality by either not showing a control button, e.g. a touchscreen control button, for the component or by disabling the control button for controlling the component. Further, control system 50 may be programmed to indicate to the user that the control button has been disabled, for example, by the showing the control button grayed out or having a X through the button (for example on a touchscreen button).

In another embodiment, where a user is a junior or temporary caregiver, control system 50 is programmed to not allow or limit certain functionality. For example, after a user has logged in or is associated with apparatus 10 and control system 50 has read or received information about the user, which includes information about the users status as a caregiver, as described above, control system 50 may be programmed to not allow a user to control or modify or implement care protocols at apparatus 10. Care protocols include, for example, the bed height, the head of bed (HOB) angle, turning, vibration or percussion treatment. Control system 50 is programmed to not allow the user to control or modify or implement care protocols by either not generating a control button to modify a care protocol or showing a disabled control button for a care protocol, as described above. Alternately, control system 50 is programmed to create a separate set or display screen of user interfaces based on the status of the caregiver.

In yet another embodiment, control system 50 is programmed to access (e.g. by reading or receiving) staff training records (from an electronic records system) for a user after the user has logged in or has become associated with apparatus 10. Based on the user's qualifications/training, control system 50 is programmed to only activate functions (by generating or enabling control buttons for those functions) that the user is trained on or qualified to operate.

In one embodiment, control system 50 is programmed to monitor hospital protocols, for example, via the hospital network or EMR/EHR system. Based on the hospital protocols, control system 50 may be programmed to update or add a protocol to apparatus 10. Hospital protocols may include specific care for a specific type of patient with a risk factor (e.g. risk of falling, risk of developing a pressure ulcer). For example, for a patient with a fall risk, the protocol may indicate that 2 or 4 of the side rails must be in their raised position or that the bed must be in a low height position. For example, when a hospital changes its rounding protocol or adds a rounding protocol, control system 50 is programmed to monitor the hospital's protocol and update its protocols to either add a rounding protocol (e.g. by adding a rounding documentation user input device, such as a button) or modify its exiting rounding documentation user input device so that it conforms to the current hospital rounding protocol.

Additionally, control system 50 may be programmed to allow a user to override the newly added or updated protocol. For example, control system 50 may provide a user input device (e.g. a button at interface 56 such at display 66) that allows the user to modify the updated protocol or select another protocol from a menu of protocols. For example, control system 50 may generate user input devices to adjust or select parameters for a given protocol, optionally with the updated protocol forming the default protocol unless otherwise modified or overridden.

In another embodiment, control system 50 is programmed to set functionality limits, e.g., maximum bed height, maximum trend, reverse trend angle, minimum and/or maximum therapy times, weight limits required for specific functionality, etc. based on a condition of a patient ("patient-specific condition").

As described above, after a patient is associated with apparatus 10 (and control system 50 has read or retrieved patient information about the patient based on the patient's ID), control system 50 (based on the patient information) determines whether the patient has a patient-specific condition and, further, optionally whether there are any hospital protocols associated with the patient-specific condition. For example, control system 50 may read or retrieve the hospital protocols for the patient-specific condition from the same electronic records system as the patient information or from another electronic records system, such as on a hospital server through the hospital network. After receiving or reading the hospital protocol for the patient-specific condition, control system 50 activates bed monitoring features, such as iBed Awareness, based on those conditions.

For example, if a patient is a fall risk, control system 50 is programmed to update or download the associated hospital protocol for the bed's configuration based on that type (and/or level of) risk. A hospital protocol for a fall risk patient may require the head end and foot end side rails to be up, the bed exit to armed, the brakes to be on, and/or the bed to be in low height position.

In another example, if a patient is on a ventilator, control system 50 is programmed to update or download the associated hospital protocol for the bed's configuration based on that condition. For example, for a patient on a ventilator, the hospital protocol may require that the head of the bed (HOB) angle is at or above 30 degrees.

In another embodiment, after a patient is associated with apparatus 10 and control system 50 has read or retrieved information about the patient based on the patient's ID, which includes one or more patient-specific conditions, control system 50 is programmed to download settings and configurations for apparatus 10 based on those conditions. For example, if control system 50 reads or retrieves a care plan for a patient, such as for an ICU patient, control system 50 downloads the care plan and configures apparatus 10 to conform to the care plan.

As described above, information about a patient, including a care plan, may be downloaded from one or more electronic records systems, such as an EHR system. For example, a care plan may include care protocols, such as patient turning, oral care, etc. Control system 50 optionally generates protocol reminders, such as described in U.S. Pat. No. 7,690,059, which is commonly owned by Stryker Corporation of Kalamazoo, Mich. and is incorporated by reference herein in its entirety, based on the care plan. For example, control system 50 may generate an icon at display 66 for the prescribed protocol or protocols and set the time periods for reminding a caregiver to perform the protocol on the patient.

In one embodiment, control system 50 is programmed to re-configure the user interface (56) and usage characteristics of apparatus 10 based on a patient-specific care condition. Optionally, control system 50 may be programmed to download a software application or applications, for example, from a $3^{rd}$ party system, which enables the reconfiguring of apparatus 10. For example, the control system 50 may configure the apparatus 10, e.g. a generic bed as a MedSurg bed or ICU bed, by enabling functions at apparatus 10 normally associated with a MedSurg bed or ICU bed. These functions may include a bed exit system; brake status monitoring; monitoring the height of the bed, including a low height position; monitoring the side rail positions; monitoring the angle of the head section ("HOB"); detection systems for detecting immersion of a patient into the mattress, pressure, patient movement (and tracking the patient movement); and sensing and monitoring patient turning, moisture in the mattress, temperature of the patient or interface with the mattress, or patient vital signs. Other functions may include providing communication with other beds or devices or remote locations, such as a nurse call system, a hospital network, or third party servers, for example; detecting location, for example, for tracking the location of the bed and/or patient.

Further yet, other functions that may be enabled by one or more software applications include expanding or modifying control functions over the various devices, such as actuators on the bed. For example, the bed actuators may be controlled to move the deck in a Trendelenburg or reverse Trendelenburg position or in a chair configuration.

Other functions may include expanding functions of an existing device or mechanism. For example, if a bed has a powered fifth wheel, such as a Zoom system availability from Stryker Corporation, the software may include updates or expansion of its functionality.

For examples of the various functions that may be incorporated into a bed, with hardware, such as actuators and/or sensors, already existing on the bed or retrofit into the bed, to transform the bed into another type of bed, such as from a generic bed to a MedSurg or ICU bed, reference is made to U.S. Pat. No. 7,690,059 (P102A); U.S. Pat. No. 7,472,439 (P107A); U.S. Pat. No. 7,702,481 (P108A); U.S. Pat. No.

8,689,376 (P113A); U.S. Pat. No. 7,779,493 (P114A); U.S. Pat. No. 7,598,353 (P188A); U.S. Pat. No. 8,413,271 (P190A); U.S. Pat. No. 8,544,126 (P199A); U.S. Pat. No. 7,699,784 (P204A); U.S. Pat. No. 8,442,738 (P243); and U.S. Pat. No. 9,149,190 (P399B), which are incorporated by reference herein in their entireties. Also, references is made to U.S. Pat. App. Ser. Nos. 62/236,452 (P490) filed Oct. 2, 2015; 62/253,167 (P491) filed Nov. 10, 2015; 62/186,464 (P482) filed Jun. 30, 2015; 62/166,354 (P465), filed May 26, 2015; 62/145,276 (P464) filed Apr. 9, 2015; Ser. No. 14/406,698 (P460) filed Dec. 9, 2014; Ser. No. 14/819,844 (P438) filed Aug. 6, 2015; Ser. No. 13/570,934 (P379) filed Aug. 9, 2012; and Ser. No. 13/802,992 (P397) filed Mar. 14, 2013, for additional functionality that may be added to the bed via one or more software applications and which are incorporated by reference herein in their entireties.

In another embodiment, control system 50 is programmed to download and execute a $3^{rd}$ party user-interface and/or other applications on the device, e.g., EHR flowsheet applications.

In some embodiments, as described above, the user interface may be a separate device from the medical apparatus, such as a phone, a watch, a tablet, a desktop or laptop computer, or a secondary medical device, which is securely connected to the medical apparatus, or may comprise a display at the medical apparatus that is mirrored to another device, such as a phone, a watch, a tablet, a desktop or laptop computer, or a secondary medical device.

In each case, the medical apparatus may comprise a patient support, such as a hospital bed, or a medical treatment apparatus, such as ventilation equipment, a pressure cuff assembly, such as DVT assembly, a hyperbaric treatment or vacuum treatment device, or the like. The feature may be an application for a patient monitoring device, including a sensor, such as a vital signs sensor, for example, a load cell for monitoring the vital signs of a patient, an EKG, a pulse oximeter, or a sensor, such as a load cell, for monitoring patient activity, including a bed exit system, or a pressure sensor or depth sensor for monitoring interface pressure at the surface or envelopment into the surface of a patient support apparatus.

Figure 11:
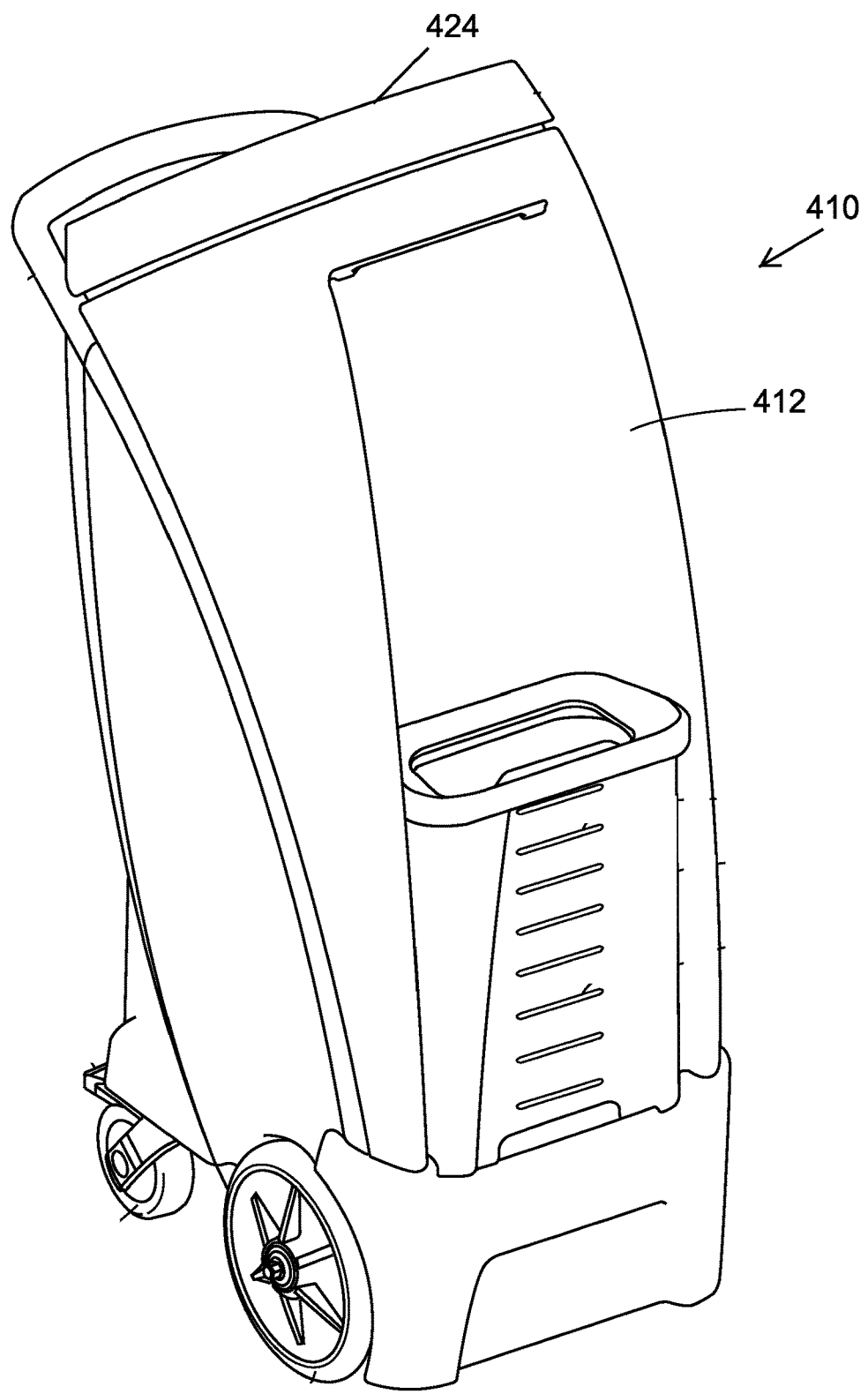
FIG. 11 is a perspective view of another embodiment of a medical apparatus in the form a temperature management apparatus.
Figure 12:
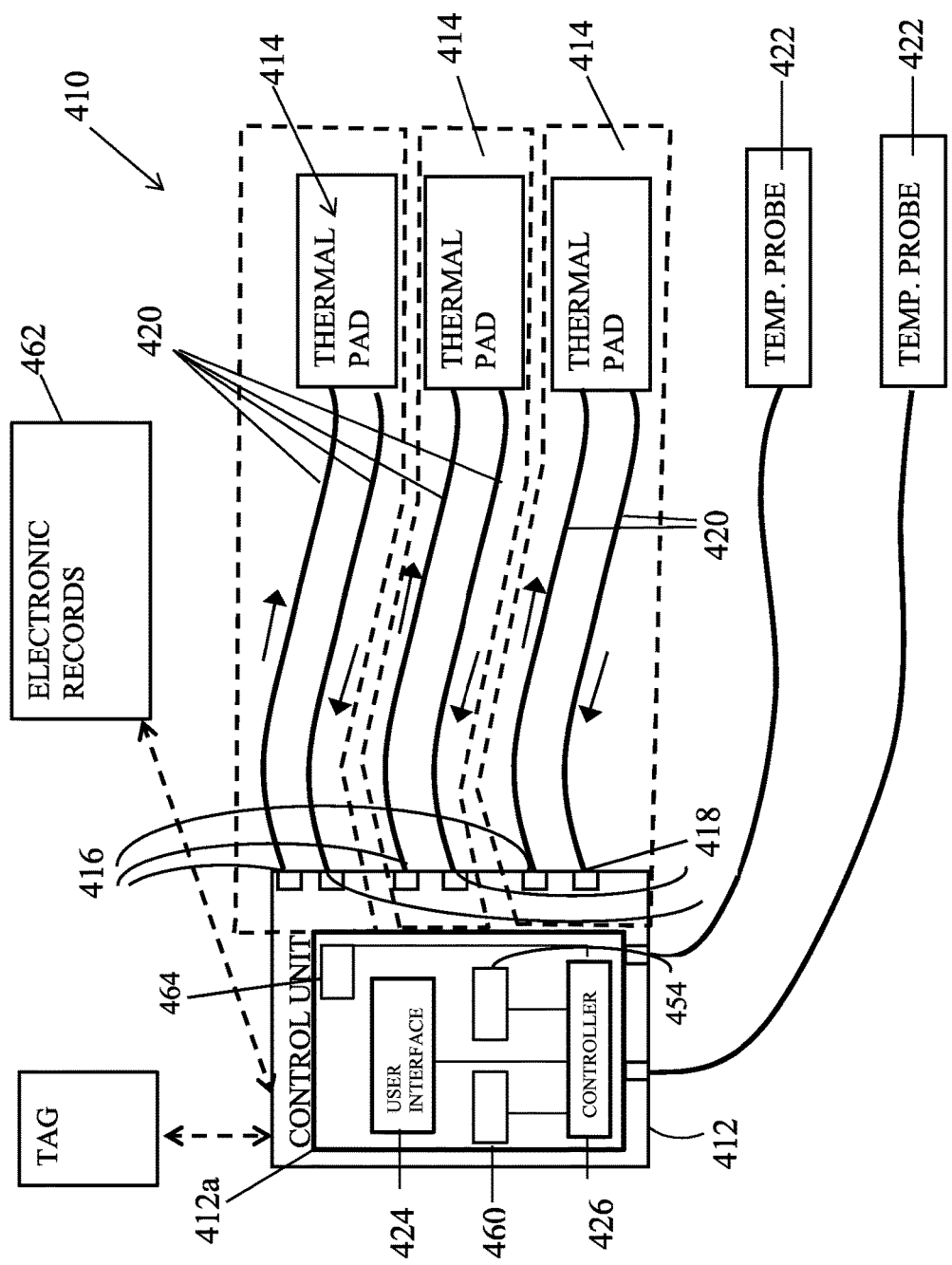
FIG. 12 is a schematic diagram of the temperature management apparatus of FIG. 11.

Referring to FIGS. 11 and 12, the numeral 410 generally designates a medical apparatus in the form of a temperature management system. Temperature management system 410 includes a thermal control unit 412 with a control system 412a and one or more thermal therapy devices, such as thermal pads 414. Control unit 412 includes a reservoir (not shown) and one or more fluid outlet ports 416 and one or more fluid inlet ports 418. Fluid outlet ports 416 and fluid inlet ports 418 are in fluid communication with a reservoir (not shown) in unit 412, which holds a fluid for circulating through the thermal pad or pads (described below), and a pump, which is controlled by control system 412a and circulates the fluid to and from the reservoir through fluid outlet ports 416 and fluid inlet ports 418. Each outlet and corresponding inlet are fluidily coupled to a respective thermal pad 414 via fluid conduits 420 to supply fluid to the thermal pad and circulate fluid back to the reservoir in control unit 412.

In order to control the temperature of the fluid circulating through the pad or pads, control system 412a optionally includes one or more temperature probes 422 in communication with controller 426. Probes 422 provide temperature information about the patient (to which the probes are attached) and allow control system 412a to adjust the temperature of the circulating fluid such that a target patient temperature can be achieved or maintained.

To operate system 410, system 410 includes a user interface 424, which is in communication with a controller 426 (FIG. 12) of control system 412a, which controls the operation of the pump based on input at user interface 424 and also, optionally, based on feedback from probes 422.

In the illustrated embodiment, control system 412a includes memory 454 in communication with the controller 426 and at least one transceiver 460 for communicating with a remote electronic records system 462, such as an EMR/EHR system, a hospital server, a third party server, including a Cloud service. Additionally, control system 412a optionally includes a reader 464, such as a barcode reader, or a near field tag reader, such as an RFID tag reader, which is in communication with controller 426.

Further, in the illustrated embodiment, control system 412a is programmed to associate a patient or a user with temperature management system 410 either based on input at user interface 424 (or at a remote user interface), for example based on a user inputting its user ID into user interface 424, or based on reading a barcode or tag worn by the user or patient, such as described above in reference to apparatus 10. Similarly, control system 412a is programmed to read or retrieve information about the user or patient from the remote electronic records system 462. Based on the information about the user or patient, control system 412a is programmed to modify or limit or disable certain functionality at system 410.

In one embodiment, control system 412a is programmed to modify its user interface 424 to disable one or more user input devices at user interface 424. For example, control system 412a may be configured to disable a user's ability to use the heating function of system 410 and limit the user to the cooling function of system 410 based on the lack of or amount of training the caregiver has completed (based on the information read or retrieved from the electronic records system). For example, in the case of a touchscreen user interface, control system 412a is programmed to eliminate or hide user input devices (e.g. regions on the touchscreen) associated with the disabled function, for example, the heating function system 410.

Accordingly, system 410 may configure (modify, limit or disable) its functionality based on either a user or a patient based on the association of the user or the patient with system 410. In other words, system 410 can customize itself for the user or patient based on the user or patient ID and user or patient information read or retrieved from an electronics record system or systems.

For additional details of system 410, reference is made to the temperature control system described in co-pending U.S. patent application Ser. No. 14/282,383, filed May 20, 2014 entitled THERMAL CONTROL SYSTEM, which is commonly owned by Stryker Corporation of Kalamazoo, Mich. and which is incorporated by reference herein in its entirety.

Figure 13:
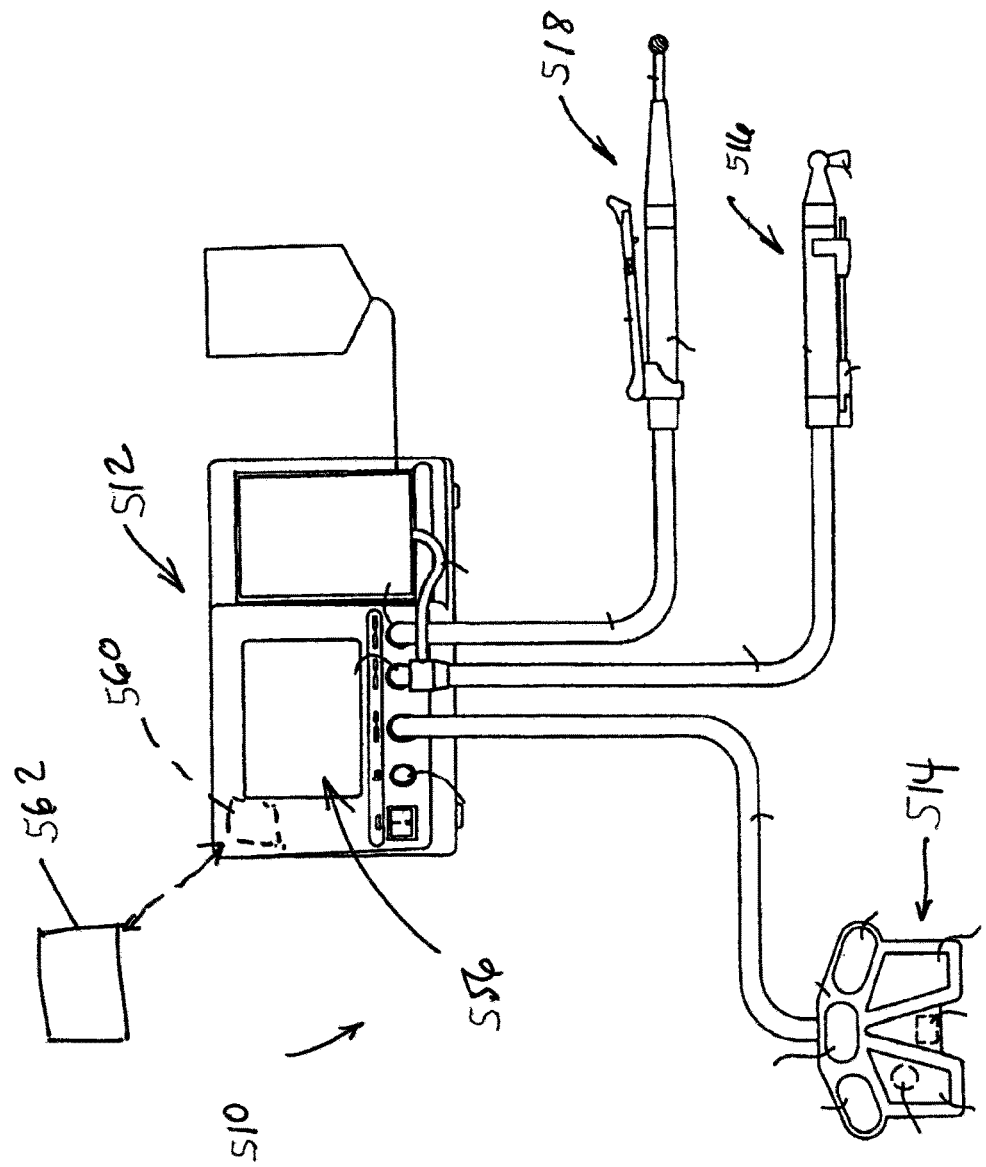
FIG. 13 is a schematic diagram of another embodiment of a medical apparatus in the form of a medical instrument.

Referring to FIG. 13, the numeral 510 generally designates another embodiment of an apparatus in the form of a surgical instrument system. Surgical instrument system 510 includes a control console 512 and a control input device 514, which control the operation of one or more surgical tools 516, 518 coupled to control console 512. Control console 512 includes a control system with a controller (not shown), a user interface 556, and a transceiver 560, which are in communication with the controller. Transceiver 560 is configured for communicating with an electronic records system 562, such as described in reference to above embodiments.

In the illustrated embodiment, the control system of control console 512 is programmed to associate a patient or a user with surgical instrument system 510 and to read or retrieve additional information about the user or patient based on the association of the patient or user with the system 510. As described above in reference to apparatus 10, system 510 may associate the patient or user with system 550 based on input at user interface 556, for example, based on a patient ID or user ID input at interface 556. Alternately, control console 512 optionally includes a reader, such as a barcode reader or a near field tag reader (such as an RFID tag reader), to read the patient ID or user ID, which is included in the barcode or signal of the tag, worn by the patient or caregiver.

Based on the information retrieved or read about the user or patient, the control system is programmed to configure, modify, or limit the functionality of control console 512. For example, the control system may be programmed to set the limits of operation for surgical tools 516, 518. This may include setting a limit on the RPM of the surgical tool 516, 518 or setting a limit on the temperature at which the surgical tool 516, 518 may operate, for example, using feedback from sensors located within the surgical tool 516, 518.

In another embodiment, the control system disables one or more functions at control console 512 based on the information retrieved from the electronic records system. For example, information retrieved from the electronic records system may include information about the user, such as training, level of expertise, preferences or the like.

In one embodiment, the information retrieved from the electronic records system includes information about the patient's procedure, which may be used as input by the control system to limit or modify the operational parameters of tools 516, 518 to the particular procedure and/or to the specific patient. For example, the control system of control console 512 may be programmed to set a limit on the RPM of the surgical tool 516, 518 or to set a limit on the temperature at which the surgical tool 516, 518 may operate, for example, based on the procedure to be performed or based on the patient's condition (which would be included in the information about the patient read or retrieved by the control system).

For further details and description of the surgical instrument system 510, reference is made to U.S. Pat. Nos. 6,017,354; 7,638,958; and 8,535,342, which are commonly owned by Stryker Corporation of Kalamazoo, Mich. and which are incorporated by reference herein in their entireties. For further details of optional control system components of the control system of control console 512, reference is made to the above embodiments.

Although the above embodiment is described in reference to a surgical instrument system of the type disclosed in U.S. Pat. Nos. 6,017,354; 7,638,958; and 8,535,342 that operates surgical tools, it should be understood that the invention may be used in other surgical systems and apparatuses, such as operating room tables and other operating room equipment or the like.

While the above embodiments describe that the various control systems of the above apparatuses include the software for performing the various functions associated with retrieving or reading information about the patient or the user, it should be understood that the software may also be provided in a module that is added to the control system or in a module in communication with the control system or in a software platform or platforms on an interface, such as the hospital server through the hospital network or a third-party server through the hospital network, or it may be provided by combination of both.

Various alterations and changes can be made to the above-described embodiments without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

We claim:

1. A medical system comprising:
a medical patient support apparatus, the medical patient support apparatus forming a patient support with a patient support surface for supporting a patient thereon and including a control system configured to control said patient support, said control system including a computer, and the patient support having a plurality of inactive hardware features, the inactive hardware features not having resident software;
a user input device in communication with the computer; and
the plurality of inactive hardware features in communication with the computer, the user input device configured and arranged to allow a user to select one of the plurality of inactive hardware features as a user selected feature and seek authorization for the use of the user selected feature of the patient support, and after receiving authorization the computer configured to download the software appropriate for enabling the user selected feature and enable the use of the user selected feature after the software is downloaded to change the user selected feature to an active feature, and the computer disabling the active feature when the user selected feature is no longer authorized.

2. The patient support apparatus according to claim 1, wherein the user input device is configured and arranged to allow a user to make payment, for example, through a credit card, or to initiate billing to the user or to a third party.

3. The patient support apparatus according to claim 1, wherein the inactive features comprise at least one feature selected from the group consisting of a vital signs sensor, a load cell for monitoring patient activity, a bed exit load cell, a pressure sensor for monitoring interface pressure at a support surface of the patient support, a moisture sensor, a temperature sensor, an optical sensor, a sensor for predictive analytics, and a depth sensor for measuring envelopment into the support surface of the patient support.

4. The patient support apparatus according to claim 1, wherein the inactive features include an entertainment device.

5. The patient support apparatus according to claim 4, wherein the entertainment device comprises a device selected from the group consisting of a TV, a tablet, a phone, an electronic game, a noise cancellation device, speakers, and a held-held music player.

6. The patient support apparatus according to claim 1, wherein the inactive features include a treatment device or a diagnostic device.

7. The patient support apparatus according to claim 6, wherein the plurality of inactive features includes a treatment device, the treatment device comprising a device selected from the group consisting of a turning device, a deep vein thrombosis device (DVT device), a percussion and/or vibration device, a temperature management device, a vacuum assisted device, and a hyperbaric device for delivering oxygen.

8. The medical system according to claim 1:
wherein the user input device is configured and arranged to allow the user to generate a prescription to prescribe the use or prohibit the use of the user selected feature, and in response to the prescription the computer configured to generate a request or cause a request to be generated to confirm insurance coverage of the prescription to provide the authorization based on the prescription and the confirmation of insurance coverage.

9. The patient support apparatus according to claim 8, wherein the user input device is resident at the medical apparatus or is remote from the medical apparatus and configured to communicate with the computer either wirelessly or through a wired connection.

10. The patient support apparatus according to claim 9, wherein the user input device is remote from the medical apparatus and configured to communicate with the computer through a network.

11. The patient support apparatus according to claim 9, wherein the user selected feature comprises a treatment device.

12. The patient support apparatus according to claim 11, wherein the treatment device comprises a device selected from the group consisting of a turning device, a deep vein thrombosis device (DVT device), a percussion and/or vibration device, a temperature management device, a vacuum assisted device, and a hyperbaric device for delivering oxygen.

13. The patient support apparatus according to claim 9, wherein the user selected feature comprises a structural component of the patient support.

14. The patient support apparatus according to claim 13, wherein the structural component comprises a side rail, a Fowler, a bed lift mechanism, and a patient support deck.

15. The patient support apparatus according to claim 9, wherein the user selected feature comprises a monitoring device.

16. The patient support apparatus according to claim 9, wherein the user selected feature is selected from the group of monitoring devices consisting of a vital signs sensor, a load cell for monitoring patient activity, including bed exit, a pressure sensor for monitoring interface pressure at a support surface of the patient support, a moisture sensor, a temperature sensor, an optical sensor, a sensor for predictive analytics, and a depth sensor for measuring envelopment into a support surface of the patient support.

17. A patient support apparatus comprising:
a patient support having a patient support surface configured to support a patient thereon;
a control system configured to control said patient support, said control system including a computer, and the patient support apparatus having a plurality components controlled by said computer and a plurality of inactive hardware features;
the plurality of inactive features in communication with and controlled by the computer;
the control system configured to associate the patient with the patient support apparatus wherein the computer has stored therein information about the patient and to automatically download an application to enable the use of one or more of the inactive features based on the information about the patient;
the computer being configured to enable the use of one or more of the inactive features using the downloaded software and configured to automatically bill the patient for the use of the enabled figures.

18. The patient support apparatus according to claim 17, wherein the inactive hardware feature comprises a treatment device.

19. The patient support apparatus according to claim 18, wherein the treatment device comprises a device selected from the group consisting of a turning device, a deep vein thrombosis device (DVT device), a percussion and/or vibration device, a temperature management device, a vacuum assisted device, and a hyperbaric device for delivering oxygen.

20. The patient support apparatus according to claim 17, wherein the inactive hardware feature comprises a component of the patient support.

21. The patient support apparatus according to claim 17, wherein the inactive hardware feature comprises a monitoring device.

22. The patient support apparatus according to claim 21, wherein the inactive hardware feature is selected from the group of monitoring devices consisting of a vital signs sensor, a load cell for monitoring patient activity, a bed exit load cell, a pressure sensor for monitoring interface pressure at a support surface of the patient support, a moisture sensor, a temperature sensor, an optical sensor, a sensor for predictive analytics, and a depth sensor for measuring envelopment into a support surface of the patient support.

23. A patient support apparatus according to claim 17, further comprising a user input device in communication with the computer and wherein the user input device is configured and arranged to allow a user to select one of the inactive hardware features as a user selected feature and purchase the use of the user selected feature of the patient support, and with the computer configured to enable the use of the user selected feature after the user purchases use of the user selected feature to change the user selected feature to an active feature.

* * * * *